(12) United States Patent
Chen et al.

(10) Patent No.: US 7,868,047 B2
(45) Date of Patent: Jan. 11, 2011

(54) ANTI-INFLAMMATORY AND PSORIASIS TREATMENT AND PROTEIN KINASE INHIBITION BY HYDROXY STILBENES AND NOVEL STILBENE DERIVATIVES AND ANALOGUES

(75) Inventors: Genhui Chen, Burnaby (CA); John M. Webster, North Vancouver (CA); Jianxiong Li, Port Moody (CA); Kaji Hu, Burnaby (CA); Jiang Zhu, Cupertino, CA (US); Wei Liu, Coquitlam (CA)

(73) Assignee: Welichem Biotech Inc., Burnaby, BC (CA)

( * ) Notice: Subject to any disclaimer, the term of this patent is extended or adjusted under 35 U.S.C. 154(b) by 0 days.

(21) Appl. No.: 11/949,529

(22) Filed: Dec. 3, 2007

(65) Prior Publication Data
US 2008/0139666 A1    Jun. 12, 2008

Related U.S. Application Data

(63) Continuation of application No. 10/893,863, filed on Jul. 15, 2004, now Pat. No. 7,321,050, which is a continuation-in-part of application No. PCT/CA03/01497, filed on Sep. 30, 2003, which is a continuation-in-part of application No. 10/148,863, filed as application No. PCT/CA00/01433 on Dec. 6, 2000, now abandoned, application No. 11/949,529, which is a continuation-in-part of application No. PCT/CA03/01497, filed on Sep. 30, 2003.

(60) Provisional application No. 60/173,300, filed on Dec. 28, 1999, provisional application No. 60/168,758, filed on Dec. 6, 1999, provisional application No. 60/414,632, filed on Oct. 1, 2002, provisional application No. 60/414,633, filed on Oct. 1, 2002.

(51) Int. Cl.
*A01N 31/08* (2006.01)
(52) U.S. Cl. ...................................................... 514/734
(58) Field of Classification Search ....................... None
See application file for complete search history.

(56) References Cited

U.S. PATENT DOCUMENTS 4,186,196 A * 1/1980 Lasher ........................ 424/605

(Continued)

FOREIGN PATENT DOCUMENTS

CA    2266763 A1    10/1999

(Continued)

OTHER PUBLICATIONS

Amson, R., et al. "The human protoncogene product p33pim is expressed during fetal hematopoiesis and in diverse leukemias", Proc. Natl. Acad. Sci., 86:8857-8861, 1989.

(Continued)

*Primary Examiner*—Karl J Puttlitz
(74) *Attorney, Agent, or Firm*—Oyen Wiggs Green & Mutala LLP

(57) ABSTRACT

The present invention provides novel methods of treating psoriasis, protein tyrosine kinase-associated disorders, inflammation, epidermal hyperproliferation, diabetes, immune and autoimmune diseases, eczema, and inflammatory bowel disease, inhibiting protein kinase, neutrophil activation, cell proliferation, tumour growth, metastasis, and the development of atheromatous plaque and restonosis, controlling angiogenesis, and preventing inflammatory bowel disease, using hydroxystilbenes and novel stilbene derivatives.

3 Claims, 5 Drawing Sheets

U.S. PATENT DOCUMENTS

| | | | |
|---|---|---|---|
| 4,723,028 | A | 2/1988 | Shudo |
| 4,788,304 | A | 11/1988 | Marshall et al. |
| 4,876,381 | A | 10/1989 | Lang et al. |
| 4,933,365 | A | 6/1990 | Marshall et al. |
| 5,472,715 | A * | 12/1995 | Uehara ............... 424/613 |
| 5,547,983 | A | 8/1996 | Charpentier |
| 5,556,996 | A | 9/1996 | Beard et al. |
| 6,008,260 | A | 12/1999 | Pezzuto et al. |
| 6,410,596 | B1 * | 6/2002 | Hopp et al. ............... 514/576 |
| 6,552,085 | B2 * | 4/2003 | Inman et al. ............... 514/576 |
| 6,790,869 | B2 | 9/2004 | Ghai et al. |
| 2003/0073712 | A1 * | 4/2003 | Wang et al. ............... 514/277 |

FOREIGN PATENT DOCUMENTS

| | | | |
|---|---|---|---|
| CA | 2433417 | A1 | 7/2002 |
| CA | 2501663 | A1 | 4/2004 |
| EP | 0170105 | A2 | 7/1985 |
| EP | 0558950 | B1 | 4/1996 |
| FR | 2785284 | A1 | 2/1998 |
| GB | 1465661 | A2 | 2/1977 |
| JP | 58159410 | | 9/1983 |
| JP | 07053359 | | 2/1995 |
| JP | 08337523 | | 12/1996 |
| JP | 10072330 | A | 3/1998 |
| WO | 9216486 | A1 | 10/1992 |
| WO | 9219583 | A1 | 11/1992 |
| WO | 9940056 | A1 | 8/1999 |
| WO | 9959561 | A3 | 11/1999 |
| WO | 0026167 | A1 | 5/2000 |
| WO | 0142231 | A3 | 6/2001 |
| WO | 0195859 | A3 | 12/2001 |

OTHER PUBLICATIONS

Ark, et al., "Mapping of the Pim-1oncogene in mouse t-haplotypes and its use to define the relative Map position of the tcl Loci to(t6) and T212 and the market tf(tufted)", Genomics, 10:385-389, 1991.

Bezou, et al., "Efficient synthesis of p-vinyl-trans-stilbene", Synthesis, 449-451, 1996.

Campbell, et al., "Association between b-lymphocyte membrane immunoglobulin and multiple members of the Src family of protein tyrosine kinases", Mol. & Cell. Biol., 12(5):2315-2321, 1992.

Cushman, et al., "Synthesis and evaluation of analogues of (Z)-1-(4-methoxyphenyl)-2-(3-4-5-trimethoxyphenyl) ethene as potential cytotoxic and antimitotic agents", J. Med. Chem., 33:2293-2306, 1992.

Dudek, et al., "Synthesis of ferrocenethiols containing oligo(phenylenevinylene) bridges and their characterization on gold electrodes", J. Am. Chem. Soc., 13:8033-8038, 2001.

Eicher, et al., "Synthese von bryophyten-inhalsstoffen 2. Synthesen von prenylierten bibenzyl-derivaten", Synthesis, 30:98-102, 1991.

Fang, et al., "Flavonoids and stilbenes from armand pine", Phytochem., 27(5):1395-1397, 1988.

Garcia-Garcia, et al., "The cancer chemopreventive agent resveratrol is incorporated into model membranes and inhibits protein kinase C alpha activity", Arch of Biochem & Biophys., 372(2):382-388, 1999.

Hu, et al. "Comparison of metabolites produced in vitro and in vivo by Photorhabdus luminescens, a bacterial symbiont of the entomopathogenic nematode Heterorhabditis megidis", Can. J. Microbiol. 44:1072-1077, 1998.

Jang, et al., "Cancer chemopreventive activity of resveratrol, a natural product derived from grapes", Science, 175:218-220, 1997.

Krow, et al., "Synthesis of antibiotic stilbenes using organomanganese arene complexes", J. Org. Chem., 57:4040-4043, 1992.

Laird, et al., "In vivo analysis of pim-1 deficiency", Nuc. Acids. Res., 21(20):4750-4755, 1993.

Paul, et al., "Antibiotics in microbial ecology—isolation and structure assignment of several new antibacterial compounds from the insect-symbiotic bacteria Xenorhabdus spp," J. of Chem. Ecol., 7(3):589-597, 1981.

Saris, et al., "The pim-1 oncogene encodes two related protein-serine/threonine kinases by alternative initiation at AUG and CUG", EMBO J., 10(3):655-664, 1991.

Seguineau, et al., "The Wittig-Horner reaction in heterogenous media—X: Synthesis of alpha-deuterated functional olefins using potassium carbonate with Deuterium oxide", Tetrahedron Letters, 29(4):477-480, 1988.

Syah, et al., "Andalasin A, a new stilbene dimer from Morus macroura", Fitoterapia, 71:630-635, 2000.

Thakkar, et al., "Synthesis and protein-tyrosine kinase inhibitory activity of polyhydroxylated stilbene analogues of piceatannol", J. Med. Chem., 36:2950-2955, 1993.

Treadwell, et al., "A cascade cyclization approach to schweinfurthin B", Org. Lett., 4(21):3639-3642, 2002.

Tudan, et al. "Selective inhibition of protein kinase C, mitogen-activated protein kinase, and neutrophil activation in response to calcium pyrophosphate dihydrate crystals, formyl-methionyl-leucyl-phenylalanine, and phorbol ester by O- (chloracetyl-carbamoyl) fumagillol (AGM-470;TNP-470)", Biochem. Pharm., 58:1869-1880, 1999.

Beutler, J.A., et al. "Cytotoxic geranyl stilbenes from macaranga schweinfurthii", CA 130:49807, 1998.

Majima, Tetsuro, et al., "Cis-trans isomerization and oxidation of radical cations of stilbene derivatives", J. Org. Chem., 61:7793-7800, 1996.

Ney, M., et al., "Anti-inflammatory effects of synthetic retinoids may be related to their immunomodulatory action", Dermatologica, 175:Suppl. 1, 93-99, 1987.

Shimizu, K., et al. "The inhibitory components from artocarpus incisus on melanin biosynthesis", CA 129:166112, 1998.

* cited by examiner

Effect of 3,5-dihydroxy-4-isopropylstilbene on crystal induced neutrophil activation Inhibition of fMLP-Induced Neutrophil Activation by 3,5-dihydroxy-4-isopropylstilbene Macroscopic Disease Index Scores Among Different Treatment Groups Total Microscopic Score of Intestinal Inflammatory Severity FIG. 5. Therapeutic effect of 9A and SASP on acute severe colon inflammation induced by 5% DSS in Balb/c mice. Expressed as percentage of survival mice at day 7 (n=9).

US 7,868,047 B2

ANTI-INFLAMMATORY AND PSORIASIS TREATMENT AND PROTEIN KINASE INHIBITION BY HYDROXY STILBENES AND NOVEL STILBENE DERIVATIVES AND ANALOGUES

This application is a continuation of, and claims priority to, U.S. application Ser. No. 10/893,863, now U.S. Pat. No. 7,321,050 filed 15 Jul. 2004 and issued 22 Jan. 2008, which is a continuation-in-part of, and claims priority to, International (PCT) application no. PCT/CA03/01497 filed 30 Sep. 2003, which is a continuation-in-part of, and claims priority to, abandoned U.S. application Ser. No. 10/148,863 filed Oct. 28, 2002 which is a national stage entry of International (PCT) application no. PCT/CA00/01433 filed Dec. 6, 2000, which claims priority to U.S. provisional application Ser. No. 60/173,300 filed Dec. 28, 1999, and U.S. provisional application Ser. No. 60/168,758 filed Dec. 6, 1999, each of which is hereby incorporated by reference in its entirety. This application is also a continuation-in-part of, and claims priority to International (PCT) application no. PCT/CA03/01497 filed Sep. 30, 2003, which claims priority to U.S. provisional application Ser. No. 60/414,632 filed Oct. 1, 2002, and U.S. provisional application Ser. No. 60/414,633 filed Oct. 1, 2002, each of which is hereby incorporated by reference in its entirety.

BACKGROUND OF THE INVENTION

The stilbenes isolated from Photorhabdus species bacteria are known to have antibiotic activity (Paul et al. Journal of Chemical Ecology, 7: 589-597 (1981), and Hu et al., Canadian Journal of Microbiology. 44: 1072-1077 (1998). However, these compounds have not been shown to have biological activity other than anti-microbial and nematicidal activities.

A similar compound, resveratrol, has been disclosed as having cancer preventive (Jang, et al. 1997, Science, 275, 218, U.S. Pat. No. 6,008,260) and protein kinase C inhibitory activities (Garcia-Garcia et. al., 1999). There are also many stilbene derivatives that are well-known in the art to have a wide range of activities and are widely distributed in nature. There is a growing interest in stilbene derivatives because of a range of activities that have been observed in some of the naturally occurring as well as some of the synthetic stilbenes.

It is known in the art that substitution on the various position on the two phenyl rings of the basic stilbene structure results in a great diversity of compounds, including those with one or two substituents on one or both of the phenyl rings of the stilbene structure (Shudo K., 1988, U.S. Pat. No. 4,723,028; Hensley, K. L., et al., WO99/59561, Kunihiro N., 1983, JP58159410; Genji I., 1995, JP07053359 and GB1465661) and those with three or more substituents on the phenyl rings (Koichi, S. et al., 1986, EP0170105; Shozo Y., et al., 1986, JP08337523; and Charpentier B. et al., 1992, WO92/19583). Compounds with other substitution on the phenyl ring, such as derivatives of vitamin A (Ney, U. M., et al. 1987, Dermatologica, 175:93-99) and vitamin D (WO 00/26167) are well-known in the art. Several publications (WO92/16486, WO99/40056, WO01/95859 and Cushman M. et. al. (1992, J. Med. Chem., 35:2293-2306) disclosed compounds that are derived from 3,4,5-trimethoxyl stilbene, and these compounds also showed anti-neoplastic activity and modest activity of modulating cytokines (WO01/95859).

Fang J. M. et al. (1988, Phytochem., 27(5): 1395-1397) also described a stilbene oxide that has two methoxyl groups at 3 and 5 positions, however, there is no substituent in between, and no specific applications are described for the treatment of inflammatory and/or autoimmune diseases. Syah Y. M. et al., described a new stilbene, andalasin A (2000, Fitoterapia., 71: 630-635) that shares some similarity to the compounds of the current invention. However it is a complicated natural product, and it is only demonstrated to have weak antinematodal and moderate antifungal properties. Dudek S. P. et al (2001, J. Am. Chem. Soc., 123: 8033-8038) described ferrocene-containing stilbene derivatives that also have two methoxyl groups at 3 and 5 positions, as well as a substituent in between. However, these compounds contain metal for completely different applications, and have different structural properties that are unrelated to the compounds of the current invention. Treadwell E. M. et al. described schweinfurthins that are also stilbene derivatives (2002, Org. Lett., 4: 3639-3642). These stilbenes share the structural nature of the current invention, however the substituents between the two hydroxyl groups are all related to the geranyl group, and they have only demonstrated anticancer activity.

Recently, when working on stilbene derivatives, the inventors discovered a group of stilbenes with a unique substitution pattern of two hydroxyl groups, or their derivatives, in position 3 and 5 and a substituent in between and their unexpected activities in mediating T-cell, cytokines, growth factors and inflammatory mediators. The present invention is related to these known and novel stilbene compounds, their synthesis, their unexpected activity, pharmaceutical compositions and their use for treatment of disorders associated with these activities such as many inflammatory and/or autoimmune diseases.

Inflammatory diseases, whether of a chronic or acute nature, represent a substantial problem in the healthcare industry. Chronic inflammation is considered to be inflammation of a prolonged duration (weeks or months) in which active inflammation, tissue destruction and attempts at healing are proceeding simultaneously (Robbins Pathological Basis of Disease by R. S. Cotran, V. Kumar, and S. L. Robbins, W. B, Saunders Co., p. 75, 1989). Although chronic inflammation can follow an acute inflammatory episode, it can also begin as an insidious process that progresses with time, for example, as a result of a persistent infection (e.g., tuberculosis, syphilis, fungal infection) which causes a delayed hypersensitivity reaction, prolonged exposure to endogenous (e.g., elevated plasma lipids) or exogenous (e.g., silica, asbestos, cigarette tar, surgical sutures) toxins, or, autoimmune reactions against the body's own tissues (e.g., rheumatoid arthritis, systemic lupus erythematosus (SLE), multiple sclerosis, psoriasis, inflammatory bowel disease, eczema). Chronic inflammatory diseases therefore, include many common medical conditions such as rheumatoid arthritis, restenosis, psoriasis, multiple sclerosis, surgical adhesions, tuberculosis, and chronic inflammatory lung and airway diseases (e.g., asthma, pneumoconiosis, chronic obstructive pulmonary disease, nasal polyps and pulmonary fibrosis).

Psoriasis is a common, chronic inflammatory skin disease, characterized by rapid multiplication and turnover of the epithelial cells with a consequent thickening of the epidermis, as well as inflamed swollen skin lesions covered with silvery white scaling patches and raised, inflamed, thickened and scaly lesions, which itch, burn, sting and bleed easily. It is therefore a disease characterized not only by inflammation, but also by proliferation of cells. In respect of proliferation, therefore, it has similarities to cancers, and both psoriasis and cancers can be described as proliferative diseases. In approximately 10% of patients, psoriasis is accompanied by pronounced arthropathic symptoms that are similar to the changes seen in rheumatoid arthritis. Approximately 2 to 3% of the U.S. population suffers from psoriasis, with 250,000 new cases being diagnosed each year. The compounds of the invention possess specific activity against psoriasis.

Eczema is a chronic inflammatory skin disorder, also known by terms used to describe the disorder as atopic dermatitis, neurodermatitis, disseminated lichen simplex chronicus, or atopic eczema. Atopic eczema affects 10 to 20 percent of children in Western populations. Eczema is characterized by physiologic, immuno pathologic, and pharmacological abnormalities that involve the skin. These abnormalities include: 1) a lowered threshold to itch stimuli, 2) a hypersensitivity to $\alpha$-adrenergic agonists and to cholinergic agents, 3) a very dry hyperkeratotic skin which has decreased water-holding capacity, 4) a marked tendency to produce lichenification in response to friction and scratching, and 5) a tendency for the skin to be colonized with bacteria.

Inflammatory bowel disease (IBD) comprises ulcerative colitis and Crohn's disease, both of which exhibit common clinical features including chronic, relapsing inflammation of the gastrointestinal tract, abdominal pain, abdominal mass, persistent diarrhea, blood loss, fever, malnutrition, and fatigue. The prognosis in IBD is unpredictable; patients may relapse several times per year or may not relapse for several years. In addition, there are many systemic complications that accompany this disease with the most common being arthritis. Symptoms of arthritis occur in one fourth of all people with IBD. Joint inflammation occurs most often when the colon is involved in the disease process and flares when the bowel disease is most active. This form of inflammatory arthritis does not cause permanent deformity and is often short lived. Other complications of this disease include eye inflammation (iritis, conjunctivitis and episcleritis), mouth inflammation (mucositis), skin inflammation (erythema nodosum and pyoderma gangrenosum), musculoskeletal abnormalities (ankylosing spondylitis), renal complications (kidney stones and fistulas to urinary tract), gallstones and other diseases of the liver (e.g. hepatitis) and biliary system (sclerosing cholangitis). Unfortunately, in many cases, long-term disease (>10 years) can lead to more severe complications such as colonic cancer and extraintestinal carcinomas. The precise etiology of these diseases remains unclear. However, it is now recognize that IBD results from dysregulation of the immune system with many facets resembling other auto-immune diseases that involve cytokines such as IFN-$\gamma$ and TNF-$\alpha$. Currently, approximately 2 million people in the United States suffer from IBD with males and females affected equally.

Protein kinase is implicated in many diseases, including cancers, as well as being a factor in diabetes, atheromatous plaque and epidermal proliferation (including psoriasis). The compounds of the invention possess specific protein kinase inhibiting activity. It is believed that protein kinase inhibitors may be of great importance in the control of uncontrolled cellular reproduction, i.e. in cellular reproduction disorders. For example DNA-PK is a serine/threonine protein kinase that is composed of a very large catalytic polypeptide and a DNA binding/targeting regulatory subunit (Ku autoantigen). Ku was first recognized as a heterodimeric (p70/p80) nuclear phosphoprotein that reacted with sera from patients suffering from autoimmune diseases lupus erythematosus and scleroderma polymyositis. Casein kinase II (Ck2) is a serine/threonine kinase that phosphorylates acidic proteins such as casein. Ck2 has been shown to play multiple roles inside the cell and can be activated by numerous growth factors, hormones and cytokines. Ck2 has multiple substrate targets inside the cell which are ultimately involved in the regulation of DNA, RNA and protein synthesis. Ck2 plays a role in controlling mitogenic signalling and neuritogenesis. Ck2 has been shown to be involved with numerous disease states. Elevated Ck2 levels have been demonstrated in solid human tumors and rapid proliferating non-neoplastic tissue such as colorectal mucosa. Ck2 activity was much higher in metastatic melanoma and in cells transformed by human cytomegalovirus. Infection of animals with protoxoan parasite resulted in fatal lymphoproliferative syndrome that is associated with the over expression of Ck2. Ck2 activity has also been demonstrated to be elevated in Alzheimer's disease.

Amson et al. (1989. Proc. Nat. Acad. Sci. 86: 8857-8861) showed that the 33-kD product of the PIM gene is highly expressed in the liver and spleen during fetal hematopoiesis. In contrast, it is only slightly expressed in circulating granulocytes in adults. It was overexpressed in hematopoietic malignancies, particularly in myeloid and lymphoid acute leukemias. The results implied a physiologic role of the Piml oncogene during hematopoietic development and a deregulation of the gene in various leukemias. Saris et al. (1991. EMBO J. 10: 655-664) provided evidence that both the murine and the human Piml gene products are protein-serine/threonine kinases. In the mouse, at any rate, they showed that the gene encodes both a 44- and a 34-kD protein, the former being an amino-terminal extension of the latter which is synthesized by alternative translation initiation at an upstream CUG codon. Ark et al. (1991. Genomics 10: 385-389) provided refined mapping of the Pim-1 locus in the mouse and used the Pim-1 gene as a marker for further genetic analysis of t-haplotypes on mouse chromosome 17. To understand the function of Pim-1 and its role in hematopoietic development, Laird et al. (1993. Nucleic Acids Res. 21: 4750-4755) generated mice deficient in Pim-1 function. Pim-1-deficient mice were ostensibly normal, healthy, and fertile; however, detailed analysis demonstrated a correlation of Pim-1 deficiency with erythrocyte microcytosis, whereas overexpression of Pim-1 in transgenic mice resulted in erythrocyte macrocytosis.

Recent studies on the molecular basis or neoplastic transformation have identified a family of genes, designated oncogenes, whose aberrant expression causes tumorigenesis. For example, the RNA tumour viruses possess such an oncogene sequence whose expression determines neoplastic conversion of infected cells. The tyrosine kinase Lck is expressed primarily in different types of hematopoietic cells. The Lck protein is found in thymocytes and mature T cells and has been reported to be expressed in mature mouse splenic B cells. Campbell et al. (1992. Mol. Cell. Biol., 12: 2315). Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a particularly preferred embodiment of the present invention.

Accordingly, a specific inhibitor of these kinases can be useful in investigating the mechanism of cancerogenesis, cell proliferation, differentiations and autoimmunology and it can be effective in prevention and chemotherapy of cancer and other pathological proliferative conditions. Hence the compounds according to the present invention can be useful in the treatment of pathological proliferation and autoimmune disorders in mammals, including humans. A human or animal, e.g. a mammal, can thus be treated by a method comprising the administration thereto of a therapeutically effective amount of one of the compounds of the invention. Amelioration of the disease state or disorder from which the human or animal is suffering can be achieved. Typical examples of such disorders are benign and malignant tumours, including leukaemia such as myeloblastic leukaemia, lymphoma, sarcoma, neuroblastoma, Wilm's tumour, malignant neoplasm of the bladder, breast, lung or thyroid and neoplasias of epithelial origin, such as mammacarcinoma. Moreover, they can be useful in the treatment of epidermal hyper-proliferation, such as psoriasis. The compounds of the invention can also be useful in inhibiting the development of atheromatous plaque and restenosis, in the control of angiogenesis, as anti-metastatic agents and in treating diabetic complications. They have also utility in the control of immune system diseases, e.g. as immuno-suppressants.

Cytokines, such as interferon-γ (IFN-γ) and tumor necrosis factor alpha (TNF-α) play major roles in inflammation. Overproduction of TNF-α and IFN-γ has been linked to several inflammatory diseases including psoriasis, eczema, inflammatory bowel disease (IBD) and rheumatoid arthritis. In psoriasis, the skin plaques of patients with psoriasis contain large numbers of activated T-cells as compared with normal skin. These T-cells release factors, including the cytokines which promote activation, hyper-proliferation and altered differentiation of keratinocytes thus forming the plaque. Anti-TNF drugs have been used in the treatment of rheumatoid arthritis for some time and recently, Remicade, an anti-TNF-α drug has been approved to treat inflammatory bowel diseases (IBD).

IFN-γ is produced by CD8+ T cells, a sub-group of CD4+ (Th1 type) T cells, and macrophages. This factor may be present at high levels in tissues afflicted by autoimmune processes. IFN-γ promotes a number of pro-inflammatory aspects of immune responses including the up-regulation of major histocompatibility complex (MHC) and adhesion molecule expression, cytokine (TNF-α) formation and the release of chemical mediators (e.g. nitric oxide). For a number of autoimmune diseases, the disease-associated inflammatory process is associated with an increased availability of IFN. IFN-γ increases endothelial cell adhesion molecule expression and thereby can influence leukocyte recruitment to inflammatory sites. Lupus-prone mice treated with anti-IFN-γ antibody were protected from disease development. The genetic knockout of the IFN-γ receptor prevented autoantibody production and glomerulonephritis in a lupus-prone mouse strain. Moreover, administration of IFN-γ to mice in a SLE disease model intensified disease parameters while mice given anti-IFN-γ antibody exhibited increased remission and survival. IFN-γ increased disease severity in mouse MS disease models. Neutralization of IFN-γ with antibodies or administration of IFN-γ ameliorates symptoms in various animal autoimmune models, effects that are often directly related to the stage of disease when these agents are provided. Thus, IFN-γ may have a strong impact on autoimmune disease progression or resolution, actions that may be specific for the particular condition. However, in lupus models, the neutralization of IFN-γ has a beneficial effect regardless of the time of introduction of the antibody. IFN-γ is an effective target for the treatment of psoriasis, eczema, multiple sclerosis, and IBD.

Vascular endothelial growth factor (VEGF) is a cytokine that is involved in a variety of physiological events, including induction of vascular hyperpermeability or edema. It plays a key role in the pathogenesis of many inflammatory disorders such as pulmonary hypertension and inflammatory airway diseases. VEGF is normally overexpressed in hyperproliferative diseases such as psoriasis and the levels of VEGF are substantially elevated in psoriasis. VEGF is also a key regulator in physiological angiogenesis during embryogenesis, skeletal growth and reproductive functions. VEGF also has been implicated in pathological angiogenesis associated with tumors, intraocular neovascular disorders and other conditions.

Leukotriene B4 (LTB4) is an important mediator of inflammation derived from the arachidonic acid pathway. It promotes adherence and chemotaxis of white blood cell's and degranulation and, consequently, plays an important role in the inflammatory process. LTB4 has been reported to be involved in lipopolysaccharide-induced sepsis and endotoxemia.

In a particular embodiment, the compounds of the present invention are useful for the treatment of the aforementioned exemplary disorders irrespective of their etiology, for example, for the treatment of transplant rejection, rheumatoid arthritis, multiple sclerosis, chronic obstructive pulmonary disease, inflammatory bowel disease, lupus, graft vs host disease, T-cell mediated hypersensitivity disease, psoriasis, eczema, Hashimoto's thyroiditis, Guillain-Barre syndrome, cancer, contact dermatitis, allergic disease such as allergic rhinitis, asthma, ischemic or reperfusion injury, or atopic dermatitis. Transplant rejection (graft v. host disease) and surgical adhesions are also affected by protein kinases. The protein kinase inhibition and anti-inflammatory properties of the compounds of this invention give rise to utility in surgery to reduce transplant rejection and surgical adhesions.

SUMMARY OF THE INVENTION

The present invention relates to stilbenes and their derivatives, to compositions comprising those stilbenes and stilbene derivatives, and to the use thereof in the treatment of inflammatory and autoimmune diseases, in particular, for the treatment of psoriasis, eczema and inflammatory bowel disease, and for the inhibition of protein kinases and cytokines. The invention also comprises the novel synthesis methods used to make the compounds.

DETAILED DESCRIPTION OF THE INVENTION

Figure 1:
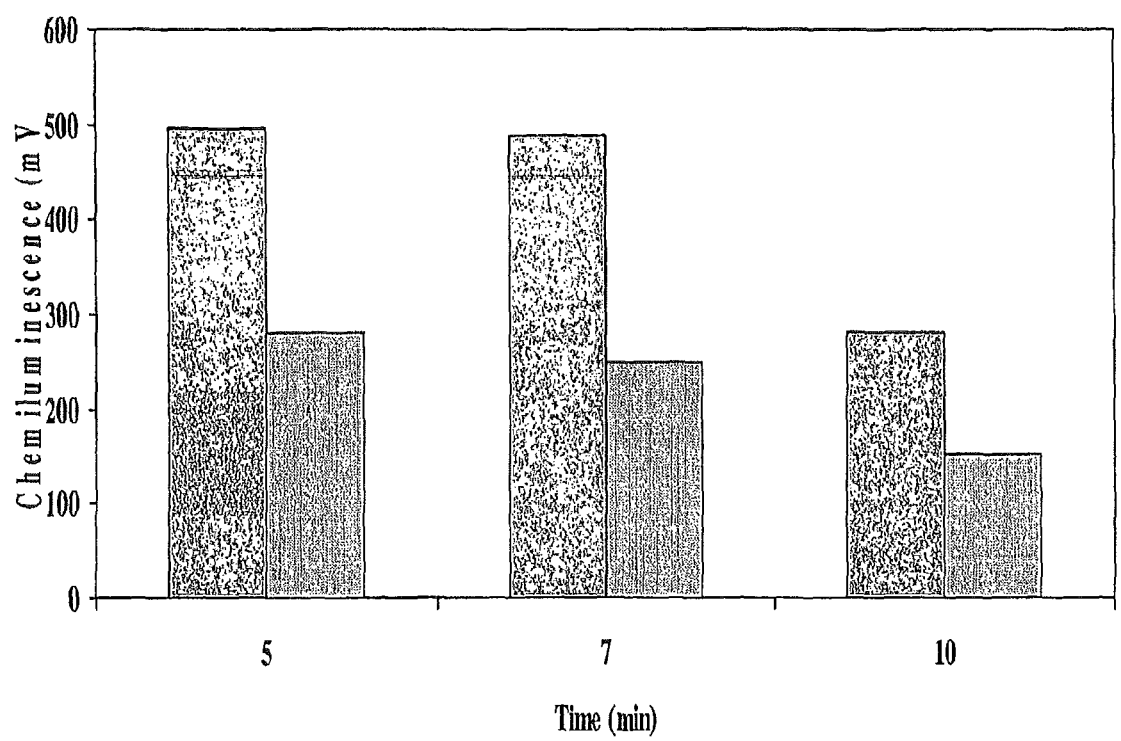
FIG. 1 is a graph showing the effect of 3,5-dihydroxy-4-isopropylstilbene on crystal induced neutrophil activation.

The invention covers new compounds of general Formula I,

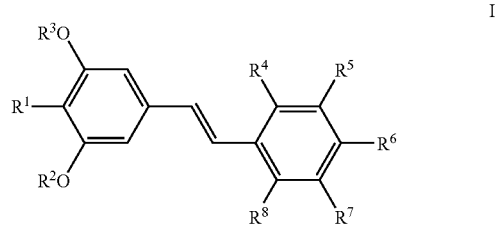

wherein $R^1$ is selected from the group consisting of unsubstituted or substituted alkyl, cycloalkyl, alkenyl, alkynyl, aryl or aralkyl group, halo, or $COR^9$;

$R^2$ and $R^3$ are independently selected from the group consisting of H, unsubstituted or substituted alkyl, cycloalkyl, aryl, aralkyl or acyl;

$R^1$, $R^5$, $R^6$, $R^7$ and $R^8$ are not H simultaneously and are independently selected from the group consisting of H, unsubstituted or substituted alkyl, alkenyl, alkynyl, aryl or aralkyl group, halo, nitro, CN, $COR^9$, $NR^{10}R^{11}$, $S(O)_2NR^{10}R^{11}$, $S(O)_nR^{10}$, n=0-2, $OR^{12}$, a cyclic, or a heterocyclic group; with the proviso that $R^6$ is not hydroxy or alkyoxy group when $R^1$ is an unsaturated group comprising of 1-3 isoprene unit(s);

$R^9$ is selected from H, unsubstituted or substituted alkyl, cycloalkyl, aryl, or aralkyl, or $NR^{10}R^{11}$, or $OR^{10}$;

$R^{10}$ and $R^{11}$ are selected from H, unsubstituted or substituted alkyl, cycloalkyl, aryl or aralkyl;

$R^{12}$ is selected from H, unsubstituted or substituted alkyl, cycloalkyl, aryl, aralkyl or acyl.

The invention also encompasses new compounds of general Formula I, wherein $R^4$, $R^5$, $R^6$, $R^7$ and $R^8$ are independently selected from the group consisting of H, unsubstituted or substituted alkyl, alkenyl, alkynyl, aryl or aralkyl group, halo, nitro, CN, $COR^9$, $NR^{10}R^{11}$, $S(O)_2NR^{10}R^{11}$, $S(O)_nR^{10}$, n=0-2, $OR^{12}$, a cyclic, or a heterocyclic group and one or more than one of $R^4$, $R^5$, $R^6$, $R^7$ and $R^8$ is F. The configuration of the double bond of the compound of Formula I is E or Z.

Highly preferred compounds include the following:

4-[2-(3,5-Dihydroxy-4-1-propylphenyl)ethenyl]benzoic acid (also called 3,5-dihydroxy-4-isopropyl-4'-carboxystilbene) (6B).

3-[2-(3,5-Dihydroxy-4-1-propylphenyl)ethenyl]benzoic acid (also called 3,5-dihydroxy-4-isopropyl-3'-carboxystilbene) (7B).

5-[2-(4-Hydroxyphenyl)ethenyl]-2-1-propyl-1,3-benzenediol (also called 3,4',5-trihydroxy-4-isopropyl-stilbene) (13B).

5-[2-(3,5-Dihydroxyphenyl)ethenyl]-2-1-propyl-1,3-benzenediol (also called 3,3',5,5'-tetrahydroxy-4-isopropyl-stilbene) (15B).

5-[2-(2-Fluorophenyl)ethenyl]-2-1-propyl-1,3-benzenediol (also called 3,5-dihydroxy-4-isopropyl-2'-fluorostilbene) (37B).

5-[2-(3-Fluorophenyl)ethenyl]-2-1-propylphenyl-1,3-diol (also called 3,5-dihydroxy-4-isopropyl-3'-fluorostilbene) (38B).

5-[2-(4-Fluorophenyl)ethenyl]-2-1-propylphenyl-1,3-diol (also called 3,5-dihydroxy-4-isopropyl-4'-fluorostilbene) (39B).

5-[2-(3,5-Difluorophenyl)ethenyl]-2-1-propylphenyl-1,3-diol (also called 3,5-dihydroxy-4-isopropyl-3',5'-difluorostilbene) (40B).

5-[2-(2,4-Difluorophenyl)ethenyl]-2-1-propyl-1,3-benzenediol (also called 3,5-dihydroxy-4-isopropyl-2',4'-difluorostilbene) (41B).

5-[2-(2,6-Difluorophenyl)ethenyl]-2-1-propyl-1,3-benzenediol (also called 3,5-dihydroxy-4-isopropyl-2',6'-difluorostilbene) (42B).

2-i-Propyl-5-[2-(2,4,6-trifluorophenyl)ethenyl]-1,3-benzenediol (also called 3,5-dihydroxy-4-isopropyl-2',4',6'-trifluorostilbene) (43B).

-[2-(2,3,4,5,6-Pentafluorophenyl)ethenyl]-2-1-propyl-1,3-benzenediol (also called 3,5-dihydroxy-4-isopropyl-2',3',4',5',6'-pentafluorostilbene) (44B).

Highly preferred compounds are 3,5-dihydroxy-4-isopropyl-4'-fluorostilbene (39B) and 3,4',5-trihydroxy-4-isopropyl-stilbene (13B).

In one preferred embodiment, this invention relates to a pharmaceutical composition comprising a compound of the following formula:

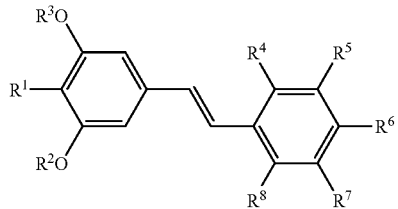

wherein $R^1$ is selected from the group consisting of unsubstituted or substituted alkyl with carbon between 1 and 18; unsubstituted or substituted cyclic alkyl with carbon between 3 and 18; alkenyl with carbon between 2 and 18; alkynyl with carbon between 2 and 18; halo, or $COR^9$;

$R^2$ and $R^3$ are independently selected from the group consisting of H, unsubstituted or substituted alkyl with carbon between 1 and 18, or acyl with carbon between 1 and 18;

$R^4$, $R^5$, $R^6$, $R^7$ and $R^8$ are independently selected from the group consisting of H, unsubstituted or substituted alkyl with carbon between 1 and 18, alkenyl with carbon between 2 and 18, alkynyl with carbon between 2 and 18, aryl or aralkyl group, chloro, bromo, iodo, fluoro, nitro, CN, $COR^9$, $NR^{10}R^{11}$, $S(O)_2NR^{10}R^{11}$, $SR^{10}$, $SOR^{10}$, $SO_2R^{10}$, $OR^{12}$;

$R^9$ is selected from H, unsubstituted or substituted alkyl, cycloalkyl, aryl, or aralkyl, or $NR^{10}R^{11}$, or $OR^{10}$;

$R^{10}$ and $R^{11}$ are selected from H, unsubstituted or substituted alkyl, cycloalkyl, aryl or aralkyl;

$R^{12}$ is selected from H, unsubstituted or substituted alkyl, cycloalkyl, aryl, aralkyl or acyl; wherein the configuration of the double bond of the compound of Formula I is E or Z;

or a pharmaceutically acceptable salt thereof, and a pharmaceutically acceptable diluent or carrier.

In a further preferred embodiment, $R^1$ is selected from the group consisting of substituted and unsubstituted alkyl with carbon between 1 to 18, substituted and unsubstituted alkenyl with carbon between 2 to 18, substituted and unsubstituted cyclic alkyl with carbon between 3 to 18, and halide.

Each $R^4$, $R^5$, $R^6$, $R^7$ or $R^8$ is independently selected from the group consisting of hydrogen, methyl, acetoxyl, hydroxyl, methoxyl, halide, acetyl and $R^2$ and $R^3$ are each independently selected from the group of acyl with carbon between 1 to 18, hydrogen and methyl groups, and the pharmaceutically acceptable salts thereof.

Preferred compounds for use in the compositions of the present invention are those compounds wherein $R^1$ is an alkyl group, $R^2$ and $R^3$ are hydrogen. Particularly preferred are those compounds wherein $R^1$ is branched short chain alkyl group, $R^2$ and $R^3$ are hydrogen. A particularly preferred compound is 3,5-dihydroxy-4-isopropylstilbene (9A).

The invention also related to the use of these compounds for treating a patient suffering from a disorder comprising immune, inflammatory or autoimmune diseases. The compounds of the invention are particularly useful against psoriasis, inflammatory bowel disease and eczema, and, in a preferred embodiment, the compound is present in a therapeutic amount.

The compounds of the invention are also useful as inhibitors of protein kinase and cytokines (such as IFN-γ and TNF-α), VEGF, LTB4 and in a preferred embodiment, the compound is present in an amount sufficient to inhibit cytokines (such as IFN-γ and TNF-α), VEGF, LTB4 as well as protein kinase activity.

The inventions also comprise methods of treating inflammation, or treating conditions which are treatable by inhibiting protein kinase, VEGF, IFN-γ, TNF-α, LTB4, T-cell, keratinocyte proliferation, by administering a pharmaceutically effective amount of the compounds of the invention. These disorders include psoriasis, eczema and IBD.

This invention also relates to novel compounds and compositions containing a compound of the Formula II:

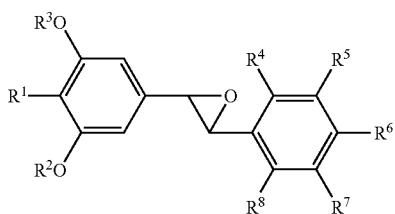

wherein $R^1$ is selected from the group consisting of unsubstituted or substituted alkyl with carbon between 1 and 18; unsubstituted or substituted alkenyl with carbon between 2 and 18; unsubstituted or substituted cycloalkyl with carbon between 3 and 18; unsubstituted or substituted alkynyl with carbon between 2 and 18; halo; alkoxy with carbon between 1 and 18; acyl group with carbon between 1 and 18;

$R^2$ and $R^3$ are independently selected from the group consisting of H, unsubstituted or substituted alkyl with carbon between 1 and 18 or acyl with carbon between 1 and 18;

$R^4$, $R^5$, $R^6$, $R^7$ and $R^8$ are independently selected from H, unsubstituted or substituted alkyl with carbon between 1 and 18; unsubstituted or substituted alkenyl with carbon between 2 and 18; unsubstituted or substituted cycloalkyl with carbon between 3 and 18; unsubstituted or substituted alkynyl with carbon between 2 and 18; unsubstituted or mono-substituted or di-substituted amino group carbon between 1 and 18; nitro; halo; carboxy; acyloxy with carbon between 1 and 18; alkoxy with carbon between 1 and 18; hydroxy; acyl group with carbon between 1 and 18;

wherein the configuration of the epoxide part of the compound can be either (R,S), (S,R), (S,S) or (R,R).

In addition to the free bases of Formula I and II, the pharmaceutically acceptable salts and the like are contemplated as being within the scope of this invention.

The compounds of this invention and the inventive compositions encompass both the trans and cis stereochemical forms of the compounds, and mixtures of the trans and cis forms. For the epoxides, the inventive compositions also encompass all stereoisomers, (R,S), (S,R), (S,S) and (R,R).

As used herein "-alkyl" means a straight chain or branched non-cyclic hydrocarbon having from 1 to 18 carbon atoms, while "lower alkyl" has the same meaning but only has from 1 to 6 carbon atoms. Representative straight chain alkyls include -methyl, -ethyl, -n-propyl, -n-butyl, -n-pentyl, -n-hexyl, -n-heptyl, -n-octyl, -n-nonly and -n-decyl; while branched alkyls include -isopropyl, -sec-butyl, -isobutyl, -tert-butyl, -isopentyl, 2-methylbutyl, and the like.

As used herein "-alkenyl" means a straight chain or branched non-cyclic hydrocarbon having from 2 to 18 carbon atoms and including at lease one carbon-carbon double bond. Representative straight chain and branched alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hezyl, 2-hexyl, 3-hexyl, and the like.

As used herein "-alkynyl" means a straight chain or branched non-cyclic hydrocarbon having from 2 to 18 carbon atoms and including at lease one carbon-carbon triple bond. Representative straight chain and branched alkynyls include -acetylenyl, -propynyl, -1-butynyl, -2-butynyl, -1-pentynyl, -2-pentynyl, -3-methyl-1-butynyl, and the like.

As used herein "-cycloalkyl" means a saturated cyclic hydrocarbon having from 3 to 18 carbon atoms. Representative cycloalkyls include -cyclopropyl, -cyclobutyl, -cyclopentyl, -cyclohexyl, -cycloheptyl, -cyclooctyl, -cyclononyl, and -cyclodecyl. Cycloalkyls also include bi- and tri-cyclic ring systems having from 8 to 18 carbon atoms such as a cycloalkyl (such as cyclopentane or cyclohexane) fused to one or more aromatic (such as phenyl) or non-aromatic (such as cyclohexane) carbocyclic rings.

As used herein "-cycloalkenyl" means a cyclic hydrocarbon having at least one carbon-carbon double bond in the cyclic system and from 5 to 18 carbon atoms. Representative cycloalkenyl include -cyclopentenyl, -cyclopentathenyl, -cyclohexenyl, -cyclohexadienyl, cycloheptenyl, cycloheptadienyl, cycloheptatrienyl, cyclooctenyl, cyclooctadienyl, cyclooctatrienyl, cyclooctatetraenyl, and the like. Cycloalkenyls also include bi- and tri-cyclic ring systems having from 8 to 18 carbon atoms such as a cycloalkenyl (such as cyclopentene or cyclohexene) fused to one or more aromatic (such as phenyl) or non-aromatic (such as cyclohexane) carbocyclic rings.

As used herein "-halogen" or "-halo" or "-halide" means fluorine, chlorine, bromine or iodine.

The compounds of this invention may be synthesized using general procedures disclosed in Example 1 with specific modifications. Examples given herein are illustrative only, and are not considered as limitations of this invention. In general, the stilbene structures of the compounds of the invention are constructed via Wittig olefination (Scheme 1) and Heck reaction (Scheme 2). The corresponding 1,3-benezendiol can be obtained by a deprotection reaction.

Scheme 1. Wittig olefination:

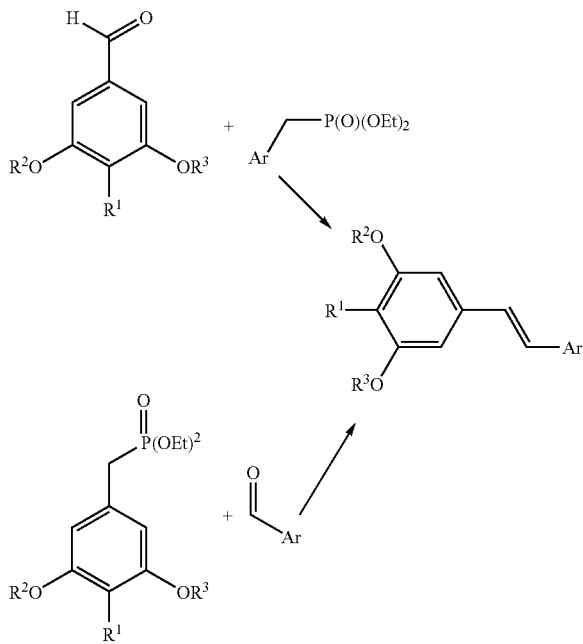

Scheme 2. Heck reaction:

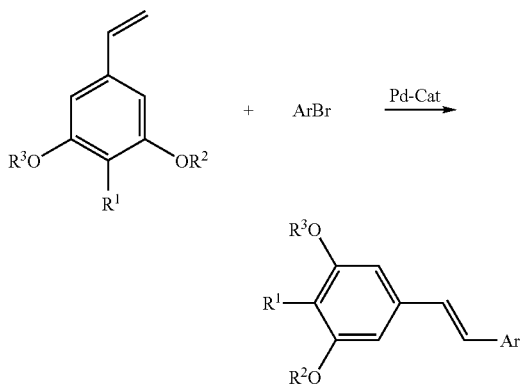

Scheme 3. Modification:

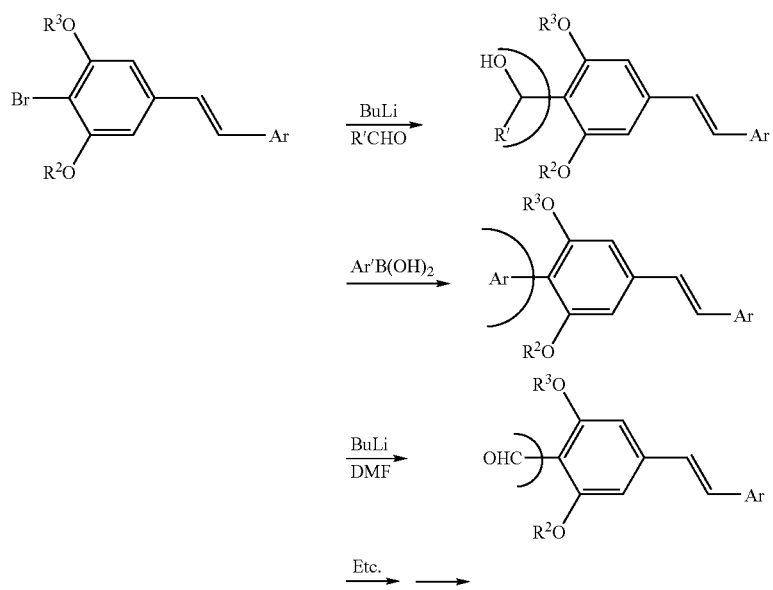

One modification of R[1] is to start with a bromostilbene (Scheme 3). The bromide can be converted to other functional groups by Suzuki coupling or a bromo-lithium exchange followed by reacting with an electrophile.

The compounds utilized in accordance with the present invention have Z or E configuration of the double bonds resulting in trans and cis isomers. The scope of the present invention is intended to cover all such isomers as well as mixtures of cis and trans isomers.

A pharmaceutically acceptable salt may be prepared for any compounds in this invention having a functional capability of forming such salt. Pharmaceutically acceptable salts may be formed with inorganic and/or organic acids and bases. Suitable acids include, for example, hydrochloric, sulfuric, nitric, benzenesulfonic, acetic, maleic, tartaric and the like, which are pharmaceutically acceptable. While pharmaceutically acceptable salts are preferred, particularly when employing the compounds of the invention as medicaments, other salts find utility, for example, in the production of these compounds, or where non-medicament-type uses are contemplated.

Compounds of the present invention have shown a range of immune-modulating activities that are demonstrated and confirmed in the forthcoming examples. Compounds which have immune-modulating activity are well-known in the art, and are described in numerous patents and scientific publications. It is generally known and accepted in the art that immune-modulating activity is useful for treating numerous diseases and conditions of animals, including humans. It is generally known in the art that pharmaceuticals having a compound or compounds with immune-modulating activity, such as those disclosed herein, as the active ingredient are useful agents for the treatment of disorders such as: clinical transplants (such as organ transplant, acute transplant or heterograft or homograft (such as is employed in burn treatment) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; IBD, including ulcerative colitis and Crohn's disease; lupus (systemic lupus erythematosis); graft vs. host disease; T-cell mediated hypersensitivity diseases, including contact hypersensitivity, eczema, delayed-type hypersensitivity, and gluten-sensitive enteropathy (Celiac disease); psoriasis; contact dermatitis (including that due to poison ivy); Hashimoto's thyroiditis; Sjogren's syndrome; autoimmune hyperthyroidism, such as Graves' Disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis, serum sickness; uticaria; allergic diseases such as respiratory allergies (asthma, hay fever, allergic rhinitis) or skin allergies; scleracierma; mycosis fungoides; acute inflammatory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic sclerosis; and morphea. In particular, the activity against VEGF expression finds utility in treating cancers and VEGF associated disorders. The inhibition of LTB4 induced cell migration is useful as anti-inflammatory agents.

The present invention thus provides methods for the treatment of disorders associated with the abovementioned activities, comprising the step of administering to a subject in need thereof at least one compound of the Formula I in an amount effective therefore. The present invention also provides methods for the treatment of disorders associated with the abovementioned activities, comprising the step of administering to a subject in need thereof at least one compound of the Formula II or a mixture of a compound of Formula I and a compound of Formula II in an amount effective therefore. Other therapeutic agents such as those known to the skilled in the art may be employed with the inventive compounds in the present methods. In the methods of the present invention, such other therapeutic agent(s) may be administered prior to, simultaneously with or following the administration of the compound(s) of the present invention.

Examples of pharmaceutical compositions include any solid (tablets, pills, capsules, granules, powder, suppositories etc.) or liquid (solutions, suspensions or emulsions) in a suitable composition for oral, topical, parenteral or rectal administration. These formulations may contain the pure compound or be in combination with a carrier or some other pharmaceutically active compound. These compositions may need to be sterile when administered parenterally.

For topical use, it will be preferred to use in the form of creams, ointments, jellies, solutions or suspensions, etc., containing the compound of Formula I and/or compound of Formula II (for purposes of this application, topical application shall include mouth washes and gargles).

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to about 50 mg of the compound per kilogram of body weight per day, or alternatively about 0.5 mg to about 3.5 g per patient per day, preferably 2.5 mg to 1 g per patient per day.

The amount of active ingredient, i.e. compound of Formula I, compound of Formula II, or mixture comprising a compound of Formula I and a compound of Formula II that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material that may vary from about 5 to about 95 percent of the total composition. Dosage unit forms will generally contain between from about 1 mg to about 1000 mg, from about 10 mg to about 900 mg, from about 50 mg to about 800 mg of an active ingredient, from about 100 mg to about 600 mg, or from about 200 mg to about 400 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compositions of the present invention comprise a compound of Formula I or Formula II in a therapeutic effective amount together with a suitable pharmaceutical carrier. An therapeutically effective amount is defined as the amount of compound necessary to cause amelioration of the disease symptoms, i.e., the psoriatic lesions, eczema lesions and IBD symptoms. In the usual course of therapy, the active compound is incorporated into an acceptable vehicle to form a composition for topical administration to the affected area, or into a form suitable for oral administration, such as tablets, capsules or pills. Compositions for topical application may be exemplified by ointments, creams, lotions, solutions, suspensions, aerosols, gels, shampoos, soaps or dusting powders. Such compositions will normally be based upon standard carriers such as pharmaceutically acceptable vegetable oils and gelatin, gums and petrolatum. Other ingredients to the compositions of the present invention may be preservatives, coloring, flavoring, sweetening, thickening, suspending, dispersing, emulsifying, swelling, stabilizing, and buffering agents as required by the specific formulation. Such compositions are envisioned to contain the active ingredient in a 0.01-10% by weight amount. Compositions for oral administration, other than the dosage units mentioned above may be exemplified by lozenges, powders, granulates, solutions, suspensions, or elixirs. The required daily dosage may be administered in single or divided doses. The exact dose to be administered will, of course, be dependent upon the particular compound employed, the age and weight of the subject and the patent's individual response. Based on animal testing and comparisons with known active agents, typical doses of the compounds of Formula I for topical administration for the treatment of psoriasis, mycosis fungoides and vitiligo are contemplated to be in the range of 0.01-5 mg/kg daily. This daily amount may be administered in single or divided doses.

The invention is now described in greater detail by reference to the following non-limiting examples.

EXAMPLES

Example 1

Synthesis of Selected Inventive Compounds

Compounds of the present invention may be prepared from 3,4-dihydroxybenzoic acid and 4-bromo-3,4-dihydroxybenzoic acid. Synthesis process includes the hydroxylmethylation, ester reduction, alcohol oxidation, witting reaction (or Homer reaction or Horner-Emmons-Wadsworth reaction) and demethylation. The synthetic routes are well established and available in the art.

Additional stilbene derivatives may be obtained by standard esterification through the reaction of hydroxylated stilbene derivative and an acid or its derivative such as the corresponding salt, chloride and anhydride. This reaction is well known in the art. For example, an alcohol was added to a mixture of anhydride and pyridine at low temperature, and the mixture was left at room temperature for sufficient time to complete the reaction. After the reaction, general work up process that is known to the art gave the corresponding derivatives.

Compounds of Formula II may be produced with an appropriate oxidant, such as m-chloroperbenzoic acid, and hydrolysis of the corresponding compounds of Formula I. For example, 3,5-dihydroxy-4-isopropyl-trans-stilbene epoxide can be synthesized from 3,5-diacetoxy-4-isopropyl-trans-stilbene compound in Scheme 4 by reacting with m-chloroperbenzoic acid (1.2 eq.) in CH$_2$Cl$_2$ at 0° C., followed by hydrolysis. After the reaction, the general work up process is known to the art. The compounds of the present invention may alternatively be prepared from different routes reported in the literature and are incorporated herein as references. (Eicher et al., Synthesis 1991, 98-102; Krow et al., J. Org. Chem. 1992, 57, 4040-4043; Seguineru, P. and Villieras Tetrahedron Letters 1988, 29, 477-480; Thakkar et al., J. Med. Chem. 1993, 36, 2950-2955; Bezou, P.; Hilberer, A. and Hadziioannou, G. Synthesis 1996, 449-451). These methods are either using complex catalyst (Krow et al., J. Org. Chem. 1992, 57, 4040-4043) or involving many steps (Eicher et al., Synthesis 1991, 98-102).

(a) Schemes of Synthesis.

Compounds of the present inventions were synthesized from commercially available 3,4-dihydroxybenzoic acid (1A) and 4-bromo-3,4-dihydroxybenzoic acid (10A) following the route, outlined in Scheme 4 and Scheme 5.

Scheme 4: Synthetic route to compounds of Formula 1:

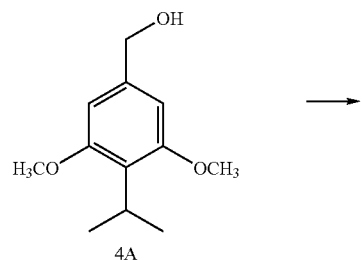

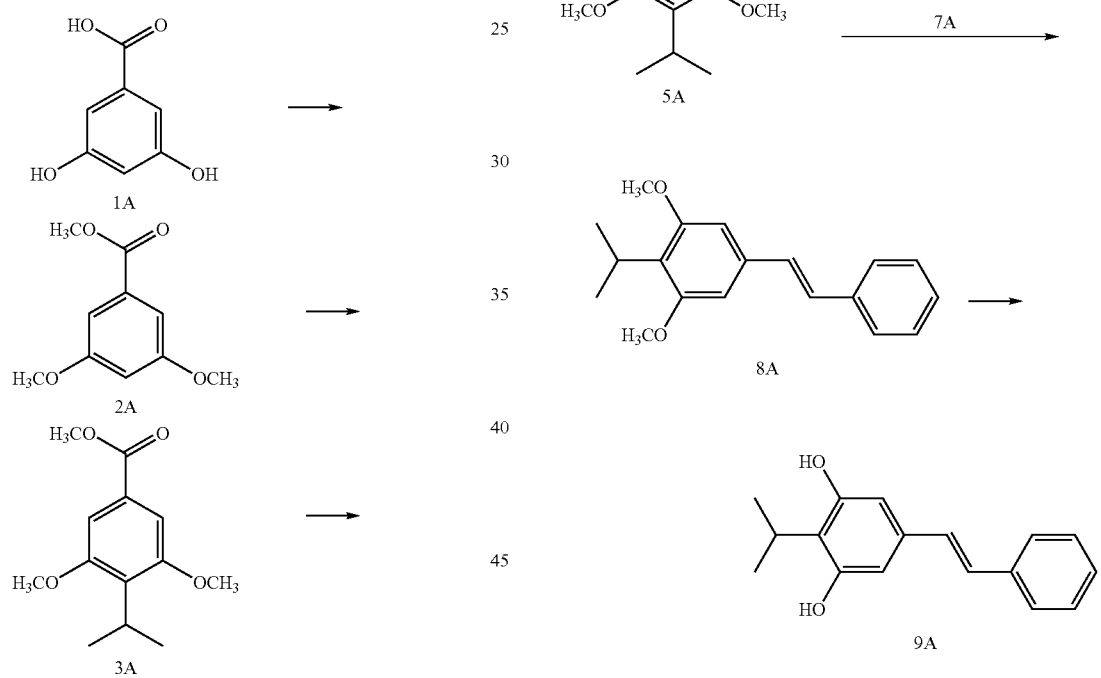

Scheme 5: Synthetic route to compounds of Formula 10:

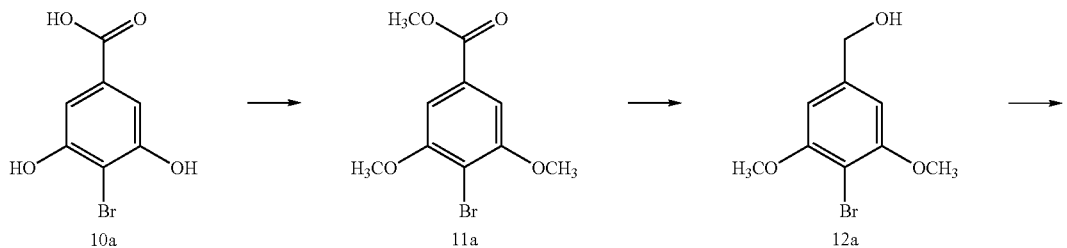

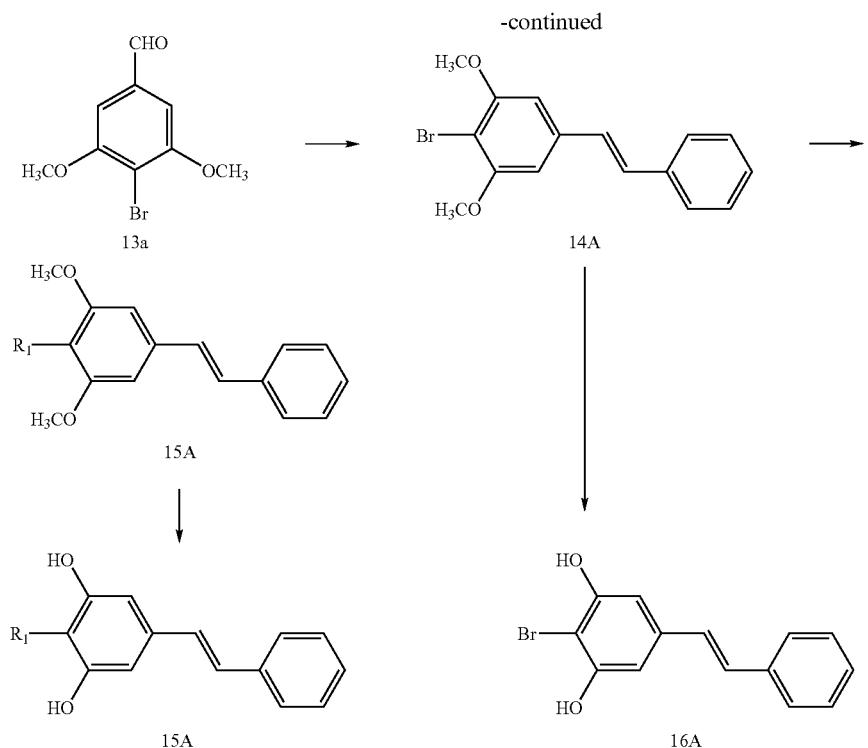

Procedure A (Methylation). Alcohol or acid (1 g, 1 eq) was added to a well stirred acetone solution (100 ml) containing dimethyl sulfate (2 eq. for each hydroxyl or carboxylic group) and $K_2CO_3$ (5 eq. for each hydroxyl or carboxylic group). This solution was refluxed for 12 hours. After filtration, solvent acetone was evaporated under reduced pressure, the residue was dissolved in EtOAc (50 mL). The EtOAc solution was washed with water (50 mL×2), saturated aqueous NaCl (50 mL), dried over $Na_2SO_4$, evaporated under reduced pressure to offer syrup which was purified by silica column chromatography (Hexanes/EtOAc=4:1). When $PO(OEt)_3$ is substituted with triphenylphosphate, cis-derivatives are synthesized.

Procedure B (Reduction of methyl ester to alcohol). $LiAlH_4$ (1.5 eq.) was added slowly with stir to the methyl ester (1 g, 1 eq) in anhydrous diethyl ether (100 mL) at 0° C. After 30 min, water (5 mL) was added slowly to the mixture to quench excess $LiAlH_4$, and the mixture was acidified with 10% HCl (aq). The organic layer was washed with water (50 mL×2), saturated $NaHCO_3$ (50 mL), dried over $Na_2SO_4$ and the solvent was evaporated under reduced pressure to offer syrup which was crystallized from EtOH/hexanes.

Procedure C (Oxidation of primary alcohol to aldehyde). Alcohol (1 g, 1 eq) in dichloromethane (10 mL) was added to a well stirred anhydrous dichloromethane (50 mL) containing suspended pyridinium chlorochromate (1.5 eq. to each hydroxyl group). After 90 min, diethyl ether (100 mL) was added, the supernatant was decanted and the black gummy syrup was washed with dry ether (20 mL×3) and became a black solid. The combined organic solution was passed through a short pad of Florisol and the solvent was removed by rotary evaporation offering syrup that was then crystallized from EtOH/hexane.

Procedure D (Wittig Reaction). NaH (2 eq.) was added to a well-stirred diethyl benzylphosphonate ester (7A) (1.5 eq.) in dry THF (25 mL) for 60 min at 0° C. Aldehyde (1 g, 1 eq) in THF (2 mL) was added slowly to the mixture, and the reaction mixture was allowed to react for 3 hours at 50° C. After cooling down to room temperature, the mixture was poured onto ice, followed by addition of 2M HCl (5 mL). The mixture was extracted with EtOAc (20 mL×3), the combined organic layer was then washed with water (25 mL×2), saturated NaCl (25 mL) and dried over anhydrous magnesium sulfate. After filtration, the solvent was evaporated under reduced pressure, the resulting syrup was purified by silica column chromatography (Pet ether/ether=8:1).

Procedure E (Demethylation): $BBr_3$ (4 mL, 1 M in $CH_2Cl_2$) in 10 ml of dry $CH_2Cl_2$ was added dropwise into methylated stilbene (1 g, 1 eq) in dry $CH_2Cl_2$ (5 mL) at −78° C., and left at room temperature overnight. The mixture was then poured on the ice and the organic layer was separated and aqueous layer was extracted with $CH_2Cl_2$ (20 mL×2). The combined organic layer was washed with saturated NaCl, dried over anhydrous sodium sulfate and evaporated under reduced pressure to dryness.

Procedure F (Acetylation). Alcohol (1 g, 1 eq) was added to an ice-cold mixture of acetic anhydride/pyridine=1:1 (vv) (5 mL), and the mixture was left at room temperature overnight. After the reaction, EtOAc (25 mL) was added to the mixture, the EtOAc was washed with ice-cold water (25 mL), ice-cold 10% HCl (25 mL×2), water (25 mL×2), saturated aqueous $NaHCO_3$ (25 mL), and dried over anhydrous $Na_2SO_4$. After removal of the solvent the product was purified by silica column chromatography (Hexanes/EtOAc=8:1).

(b) Use of Scheme 4 to make 3,5-Dihydroxy-4-isopropyl-trans-stilbene and its derivatives.

(i) Methyl 3,5-dimethoxy-benzoate (compound 2A in Scheme 4) (Procedure A): the crude product (syrup) was crystallized from EtOH/Hexanes to give pure compound 2 (Scheme 1) (~90%). Mp: 110-113° C. NMR (100 MHz, CDCl$_3$): δ 4.20 (s, 6H, OCH$_3$), 4.60 (s, 3H, COOCH$_3$), 6.30 (t, 1H, J=2.2 Hz, H-4), 7.20 (d, 2H, H-2, 6).

(ii) Methyl 3,5-dimethoxy-4-isopropyl-benzoate (compound 3A in Scheme 4): anhydrous AlCl$_3$ (0.85 g) was added to dry CS$_2$ (100 mL) containing methyl 3,5-dimethoxy-benzoate (compound 2A in Scheme 4) (0.86 g) and 2-bromopropane (0.61 mL, 1.1 eq.). This solution was heated to reflux for 7 days. The mixture was filtered, washed with water (100 mL×2), saturated NaHCO$_3$ (100 mL) and saturated NaCl (100 mL), dried over Na$_2$SO$_4$. After filtration and removal of the solvent, the crude product was purified by column chromatography (EtOAc/Hexanes=4:1) to give methyl 3,5-dimethoxy-4-isopropyl-benzoate (compound 3A) (0.69 g, 66%) that was crystallized from EtOH/Hexanes. NMR (100 MHz, CDCl$_3$): δ 1.61 (d, 6H, J$_1$', 2'=7.1 Hz, H-2'), 3.66 (hept, 1H, H-1'), 3.88 (s, 6H, OCH$_3$), 3.94 (s, 3H, COOCH$_3$), 7.25 (s, 2H, H-2, 6).

(iii) 3,5-Dimethoxy-4-isopropyl-benzyl alcohol (compound 4A in Scheme 4) (Procedure B): The crude product (syrup) was crystallized from EtOAc/Hexanes to give compound 4A (85% yield). NMR (100 MHz, CDCl$_3$): δ 1.31 (d, 6H, J$_1$', 2'=7.1 Hz, H-2'), 3.61 (hept, 1H, H-1'), 3.84 (s, 6H, OCH$_3$), 4.68 (s, 1H, H—OH), 6.60 (s, 2H, H-2, 6).

(iv) 3,5-Dimethoxy-4-isopropyl-benzaldehyde (compound 5A in Scheme 4) (Procedure C): The resulting residue was crystallized from EtOH to give pure compound 5 (80% yield). NMR (100 MHz, CDCl$_3$): δ 1.31 (d, 6H, J$_1$', 2'=7.1 Hz, H-2'), 3.61 (hept, 1H, H-1'), 3.84 (s, 6H, OCH$_3$), 4.68 (s, 1H, H—OH), 6.60 (s, 2H, H-2, 6).

(v) Diethyl benzylphosphonate ester (compound 7A in Scheme 4): Triethyl phosphite (3.2 mL, 1.5 eq.) was added to the benzyl bromide (2.11 g) containing a catalytic amount of tetrabutylammonium iodide, the mixture was heated to 110-130° C. overnight. Excess triethyl phosphite was removed by heating the solution for 1 hour at 100° C. under vacuum (15 mm Hg) to yield compound 7 quantitatively. NMR (100 MHz, CDCl$_3$): δ 1.21 (t, 6H, J$_2$', 1'=7.1 Hz, H-2'), 3.02 (s, 1H, H-α.), 3.24 (s, 1H, H-β.), 3.98 (quint, 2H, H-1'), 7.27 (s, 5H, H—ArH).

(vi) 3,5-Dimethoxy-4-isopropyl-trans-stilbene (compound 8A in Scheme 4) (Procedure D): The product was purified by column chromatography (Et$_2$O/Hexanes=1:8) and crystallized from ether/hexanes to give pure compound 8 (70% yield). Mp: 64-66° C. NMR (400 MHz, CDCl$_3$): δ 1.28 (d, 6H, J=7.0 Hz, CH$_3$), 3.58 (hept, 1H, —CH—), 3.85 (s, 6H, H—OCH$_3$), 6.69 (s, 2H, H-2, 6), 7.05 (s, 2H, CH), 7.25 (m, 1H, H-4'), 7.35 (m, 2H, H-3', 5'), 7.25 (m, H-2', 6').

(vii) 3,5-Dihydroxy-4-isopropyl-trans-stilbene (compound 9A in Scheme 4) (Procedure E): The product was purified by column chromatography (EtOAc/Hexanes) and give desired compound 9A (95% yield). Mp: 140-142° C. NMR (400 MHz, CDCl$_3$): δ1.38 (d, 6H, J=7.3 Hz, CH$_3$), 3.46 (hept, 1H, —CH—), 4.80 (s, 2H, H—OH), 6.50 (s, 2H, H-2, 6), 6.92 (d, 1H, J=16.2 Hz), 6.97 (d, 1H), 7.25 (m, 1H, H-4'), 7.34 (m, 2H, H-3', 5'), 7.52 (m, 2H, H-2', 6').

(c) Use of Scheme 5 to form Additional 4-substituted 3,5-dihydroxy-trans-stilbenes and their Derivatives.

(viii) Methyl 3,5-dimethoxy-4-bromo-benzoate (compound 11A in Scheme 5) (Procedure A). The crude product (95%) was crystallized from EtOH/Hexanes. Mp: 119-1240 C. NMR (100 MHz, CDCl$_3$): δ 3.96 (s, 3H, COOCH$_3$), 3.99 (s, 6H, OCH$_3$), 7.28 (s, 2H, H-2, 6).

(ix) 3,5-Dimethoxy-4-bromo-benzyl alcohol (compound 12A in Scheme 5) (Procedure B). The crude product (85% of yield) was crystallized from EtOH/Hexanes. Mp: 84-95° C. NMR (100 MHz, CDCl$_3$): δ 1.95 (s, 1H, OH), 3.93 (s, 6H, OCH$_3$), 4.69 (s, 1H, CH$_2$), 6.61 (s, 2H, H-2, 6).

(x) 3,5-Dimethoxy-4-bromo-benzaldehyde (compound 13A in Scheme 5) (Procedure C). The crude product (75%) was crystallized from EtOH/flexanes. Mp: 110-113° C. NMR (100 MHz, CDCl$_3$): δ 4.02 (s, 6H, OCH$_3$), 7.11 (s, 2H, H-2, 6), 9.97 (s, 1H, CHO).

(xi) 3,5-Dimethoxy-4-bromo-trans-stilbene (compound 14A in Scheme 5) (Procedure D). The crude product was purified by column chromatography (Pet ether/Ether=8:1) in 70% and crystallized from ether/hexanes. Mp: 149-152° C. NMR (400 MHz, CDCl$_3$): δ 3.96 (s, 6H, 2XOCH$_3$), 6.72 (s, 2H, H-2, 6), 7.06 (d, 1H, J=16.2 Hz, H), 7.11 (d, 1H, H), 7.28 (m, 1H, H-4'), 7.37 (m, 2H, H-3', 5'), 7.55 (m, 2H, H-2', 6').

(xii) 4-Bromo-3,5-Hydroxy-trans-stilbene (compound 16A in Scheme 5) (Procedure E): The crude product was purified by column chromatography (Pet ether/Ether=4:1) in 90% and crystallized from Ether/Hexanes. Mp: 150-152° C. NMR (100 MHz, CDCl$_3$): δ 5.39 (s, 2H, 2 X OH), 6.81 (s, 2H, ArH-2, 6), 7.06 (d, 1H, J=16.2 Hz, H), 7.11 (d, 1H), 7.28 (m, 1H, H-4'), 7.37 (m, 2H, H-3', 5'), 7.55 (m, 2H, H-2', 6').

(xiii) 3,5-Dimethoxy-4-ethyl-trans-stilbene (compound 15A-a in Scheme 5): t-butyl Li (1.1 mL, 1M in THF) was added at −78° C. to a THF solution (10 mL) containing 3,5-dimethoxy-4-bromo-trans-stilbene (0.53 g). After addition, the solution was slowly heated to reflux for 30 min and then cooled down to −78° C. Ethyl iodide (1.2 eq, 0.265 mL) was added to the solution at −78° C. After reaction finished, water (10 mL) was added dropwise to the mixture, THF was evaporated under reduced pressure. The mixture was extracted with CH$_2$Cl$_2$ (5 mL×3), the combined organic layer was dried over anhydrous magnesium sulfate, and remove under reduced pressure. The product mixture was purified by column chromatography (ether/pet ether=1:8) and gave 3,5-dimethoxy-4-ethyl-trans-stilbene (15A-a) (70%) and 3,5-dimethoxy-trans-stilbene (30%) due to the moisture. Mp: 70-73° C. NMR (400 MHz, CDCl$_3$): δ 1.12 (t, 6H, J=7.2 Hz, CH$_3$), 2.70 (q, 2H, —CH$_2$—), 3.91 (s, 6H, OCH$_3$), 6.74 (s, 2H, H-2, 6), 7.07 (s, 2H), 7.26 (m, 1H, H-4'), 7.36 (m, 2H, H-3', 5'), 7.52 (m, 2H, H-2', 6').

(xiv) 3,5-Dihydroxy-4-ethyl-trans-stilbene (compound 16A-a in Scheme 5) (Procedure E): After column chromatography (ether/pet ether=8:1) the product was obtained in 91% of yield and crystallized from ether/hexanes. Mp: 143-146° C. NMR (100 MHz, CDCl$_3$): δ 1.22 (t, 6H, J=7.5 Hz, 2×CH$_3$), 2.70 (q, 2H, CH$_2$), 4.81 (s, 2H, 2 X OH), 6.60 (s, 2H, H-2, 6), 7.00 (s, 2H), 7.26 (m, 1H, H-4'), 7.36 (m, 2H, H-3', 5'), 7.52 (m, 2H, H-2', 6').

(xv) 3,5-Dimethoxy-4-myristyl-trans-stilbene (compound 15A-b in Scheme 5). Procedure and work up are the same as compound 14 [see (xi) above]. Mp: 68-70° C. NMR (100 MHz, CDCl$_3$): δ 0.91 (m, 6H, 2 X CH$_3$), 1.29 (m, 22H), 2.65 (m, 2H, CH$_2$), 3.90 (s, 6H, 2 X OCH$_3$), 6.73 (s, 2H, H-2, 6), 7.10 (s, 2H), 7.26 (m, 1H, H-4'), 7.36 (m, 2H, H-3', 5'), 7.52 (m, 2H, H-2', 6').

(xvi) 3,5-Dihydroxy-4-myristyl-trans-stilbene (compound 16A-b in Scheme 5) (Procedure E): After column chromatography (ether/pet ether=8:1) the product was obtained in 91% of yield and crystallized from ether/hexanes: Mp: 125-128° C. NMR (100 MHz, CDCl$_3$): δ 0.95 (m, 6H, 2 X CH$_3$), 1.30 (m, 22H, 10 X CH$_2$), 2.65 (m, 2H, CH$_2$), 4.80 (s, 2H, 2 X OH), 6.60 (s, 2H, H-2, 6), 7.00 (s, 2H), 7.26 (m, 1H, H-4'), 7.36 (m, 2H, H-3', 5'), 7.52 (m, 2H, H-2', 6').

(d) Examples of Additional hydroxy-trans-stilbene Derivatives

Additional stilbene derivatives can be synthesized following well established procedures such as esterification. The epoxide, 3,5-dihydroxy-4-isopropyl-trans-stilbene epoxide was originally isolated from the bacteria, Photorhabdus luminescens spp. This compound and its derivatives may also be produced with Scheme 6:

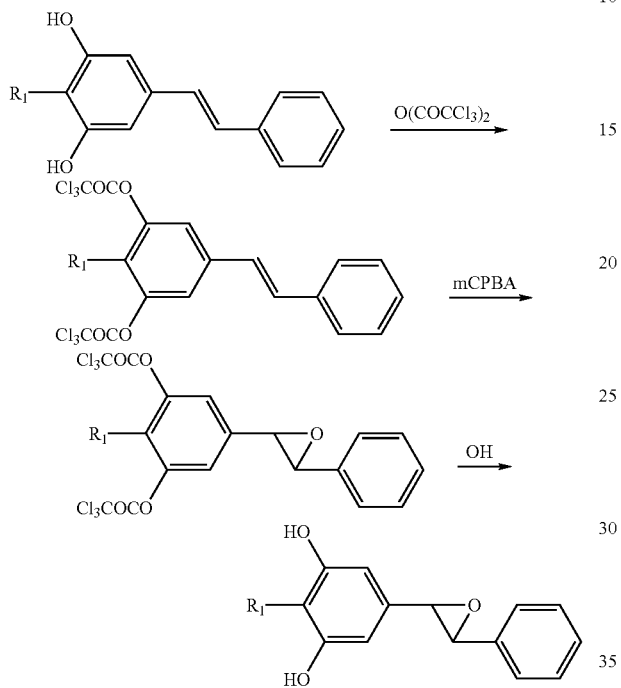

(xvii) 3,5-Di-acetoxy-4-isopropyl-trans-stilbene (Procedure E): The desired product was obtained in quantitative yield from 3,5-dihydroxy-4-isopropyl-trans-stilbene following procedure F and crystallized from ether/hexanes. Mp: 125-128° C. NMR (400 MHz, CDCl$_3$): δ 1.25, 1.27 (s, 6H, 2 X CH$_3$), 2.35 (s, 6H, 2 X COCH$_3$), 3.08 (heptet, 1H, CH), 6.99, 7.02 (s, 2H, H-2, 6), 7.06 (s, 2H), 7.26 (m, 1H, H-4'), 7.36 (m, 2H, H-3', 5'), 7.52 (m, 2H, H-2', 6').

(xviii) 3,5-Di-chloroacetoxy-4-isopropyl-trans-stilbene: Triethyl amine (2 eq. for each OH group) was added to the mixture of 3,5-dihydroxy-4-isopropyl-trans-stilbene (143 mg) and chloroacetic anhydride (4 eq.) in ether (5 mL) at room temperature and left overnight. After evaporation of the solvent, the product was purified by silica column chromatography (EtOAc/Hexanes=1:8) to give pure product that was crystallized from ether/hexanes (167 mg, 72%). Mp: 83-85° C. NMR (400 MHz, CDCl$_3$): δ 1.26, 1.33 (s, 6H, 2 X CH$_3$), 3.08 (hept, 1H, CH), 4.39 (s, 4H, ClCH$_2$CO), 6.99, 7.02 (s, 2H, H-2, 6), 7.06 (s, 2H), 7.26 (m, 11H, H-4'), 7.36 (m, 2H, H-3', 5'), 7.52 (m, 2H, H-2', 6').

(xix) 3,4',5-Tri-acetoxy-trans-stilbene (Procedure E): Following Procedure F, the desired product was obtained quantitatively from 3,4'-5-trihydroxy-trans-stilbene (100% yield). Mp: 113-116° C. NMR (400 MHz, CDCl$_3$): δ 2.30-2.35 (s, 9H, 3 X COCH$_3$), 6.82 (t, 1H, J$_{4,2}$=J$_{4,6}$=2.5 Hz, H-4), 6.99 (d, 1H, J=16.2 Hz), 7.04 (d, 1H), 7.09 (m, 1H), 7.12 (d, 1H, H-2, 6), 7.49 (m, 1H).

(xx) 3,4',5-Tri-acetoxy-trans-stilbene epoxide: m-chloroperbenzoic acid (1.2 eq.) was added to CH$_2$Cl$_2$ (1 mL) containing 3,4',5-tri-acetoxy-trans-stilbene (24 mg) at 0° C., until TLC showed the disappearance of the starting material (about 3 hours). This solution was than washed with water (1 mL×2), saturated NaHCO$_3$ (1 mL), saturated NaCl (ML) and dried over MgSO$_4$. After filtration and removal of the solvent, the syrup was purified by silica column chromatography (Hexanes/Ether=8:1) to give pure compound that was crystallized from ether/hexanes (16 mg, 64%). Mp: 133-137° C. NMR (400 MHz, CDCl$_3$): δ 2.29-2.31 (s, 9H, 3 X COCH$_3$), 3.82 (q, 2H, J$_{A,B}$=1.8 Hz, CH$_A$—CH$_B$), 6.89 (t, 1H, J$_{4,2}$=J$_{4,6}$=2.1 Hz, H-4), 6.97 (dd, 2H, H-2, 6), 7.10, 7.34.

(xxi) 3,4',5-Trimethoxy-trans-stilbene (Procedure A): The product was purified by silica column chromatography (EtOAc/Hexanes=1:8) to give pure product (~100% yield) which was crystallized form ether/hexanes. Mp: 51-54° C. NMR (400 MHz, CDCl$_3$): δ 3.83 (s, 9H, 3 X OCH$_3$), 6.38 (t, 1H, J$_4$,3=J$_4$,5=4.6 Hz, H-4), 6.65 (d, 2H, H-3, 5), 6.88-6.91 (2H, H-2', 6'), 6.91 (d, 1H, J=16.1 Hz), 7.04 (d, 1H), 7.43-7.46 (2H, H-3', 5').

(xxii) 3,4-Methylenoxy-trans-stilbene (Procedure D): Procedure D was used to synthesize the designed compound from 3,4-methylenoxynezaldehyde. The resulting syrup was purified by silica column chromatography (Ether/Hexanes=1:8) to give pure product that was crystallized form ether/hexanes (75%). Mp: 89-91° C. NMR (400 MHz, CDCl$_3$): δ 5.99 (s, 2H, —CH$_2$—), 6.80 (d, 1H, J$_{5,6}$=8.1 Hz, H-5), 6.94 (d, 1H, J$_{AB}$=16.3 Hz), 6.95 (dd, 1H, J$_6$,2=0.4 Hz, H-6), 7.03 (d, 1H), 7.08 (d, 1H, H-2), 7.24 (m, 1H, H-4'), 7.34 (m, 2H, H-3', 5'), 7.48 (m, 2H, H-2', 6').

Example 2

Synthesis of Additional Inventive Compounds

Experiment 1. 4-[2-(3,5-Dimethoxy-4-1-propylphenyl)ethenyl]benzoic acid (1B)

(a) 3,5-Dimethoxy-4-i-propylbenzyl alcohol

To a suspension of LiAlH$_4$ (95%) (5.00 g, 125 mmol) in dry ether (100 mL) at 0° C. was added a solution of methyl 3,5-dimethoxy-4-1-propylbenzoate (15.7 g, 90.1 mmol), in ether (300 mL) under N$_2$. The suspension was stirred at 0° C. for one hour then for an additional hour at room temperature. The reaction was quenched by slow addition of a saturated Na$_2$SO$_4$ aqueous solution (10 mL) at 0° C. The mixture was stirred overnight. The solid was filtered off and the filtrate was evaporated to dryness to give the desired alcohol (13.8 g, 88% yield) as white crystals. $^1$HNMR (CDCl$_3$. ppm): δ 1.34 (d, J=7.2 Hz, 6H), 3.65 (hept., J=7.2 Hz, 1H), 3.88 (s, 6H), 4.70 (s, 2H), 6.62 (s, 2H).

(b) 3,5-Dimethoxy-4-1-propylbenzyl aldehyde

A mixture of 3,5-dimethoxy-4-1-propylbenzyl alcohol (13.05 g, 62.1 mmol) and pyridinium chlorochromate (33.92 g, 157 mmol) was stirred in CH$_2$Cl$_2$ (100 mL) in the presence of K$_2$CO$_3$ (4.18 g, 30 mmol) for 30 min. Ether (300 mL) was added to quench the reaction. The mixture was passed through a short pad of Florisil and the pad was washed thoroughly with ether. Evaporation of the solvent gave 3,5-dimethoxy-4-1-propylbenzyl aldehyde (11.89 g. 92% yield)

as a yellowish crystal. ¹HNMR (CDCl₃, ppm): δ 1.32 (d, J=7.2 Hz, 6H), 3.68 (hept., J=7.2 Hz, 1H), 3.92 (s, 6H), 7.12 (s, 2H), 9.96 (s, 1H).

(c) (3,5-Dimethoxy-4-1-propylphenyl)ethene

To a suspension of methyltriphenylphosphonium bromide (6.89 g, 19.3 mmol) in THF (100 mL) under argon was added BuLi (7.7 ml, 2.5M in hexane, 19.3 mmol) at room temperature. The resultant red solution was stirred for 10 min. and then 3,5-dimethoxy-4-1-propylbenzyl aldehyde (4.02 g, 19.3 mmol) in THF (20 mL) was added. After 2 hours, the reaction was quenched with water (20 mL). The mixture was extracted with ether (3×100 mL). The extract was washed with saturated saline solution (3×30 mL) and dried over sodium sulphate. Evaporation of ether followed by flash chromatography using 3% ethyl acetate in hexane afforded pure (3,5-dimethoxy-4-1-propylphenyl)ethene (2.64 g, 66% yield) as a colorless solid. ¹HNMR (CDCl₃, ppm): δ 1.31 (d, J=7.1 Hz, 6H), 3.61 (qint, J=7.1 Hz, 1H), 3.86 (s, 6H), 5.25 (d, J=11 Hz, 1H), 5.73 (d, J=17 Hz, 1H), 6.64 (s, 2H), 6.70 (dd, J=11, 17 Hz, 1H).

(d) 4-[2-(3,5-Dimethoxy-4-1-propylphenyl)ethenyl]benzoic acid (1B)

A mixture of (3,5-dimethoxy-4-1-propylphenyl)ethene (0.303 g, 1.50 mmol), 4-bromobenzoic acid (0.269 g, 1.30 mmol, dihydrogendi-μ-chlorotetrkis (di-tert-butylphosphinito-KcP) dipalladate (0.0625 g, 0.067 mmol), Bu₄NI (0.245 g, 0.67 mmol) and K₂CO₃ (0.614 g, 4.40 mmol) in DMF (7 mL) was heated at 140° C. under argon. After the reaction was complete (5 h), the reaction mixture was poured into water (100 ml). This was washed with ether. The aqueous phase was acidified with 6NHCl and extracted with ether (2×100 mL). The extract was washed with saturated sodium chloride and then dried over anhydrous Na₂SO₄. Evaporation of ether gave the pure acid 1 (0.345 g, 71% yield). ¹HNMR (CDCl₃, ppm): δ 1.32 (d, J=7.1 Hz, 6H), 3.63 (qint, J=7.1 Hz, 1H), 3.90 (s, 6H), 6.76 (s, 2H), 7.08 (d, J=17 Hz, 1H), 7.27 (d, J=17 Hz, 1H), 7.63 (d, J=8 Hz, 2H), 8.13 (d, J=8 Hz, 2H).

Experiment 2. 3-[2-(3,5-Dimethoxy-4-1-propylphenyl)ethenyl]benzoic acid (2B)

This compound was synthesized from (3,5-dimethoxy-4-1-propylphenyl)-ethene and 3-bromobenzoic acid in 77% yield in the same way as described in preparation of 1B. ¹HNMR (CDCl₃, ppm): δ 1.32 (d, J=7.1 Hz, 6H), 3.63 (qint, J=7.1 Hz, 1H), 3.90 (s, 6H), 6.76 (s, 6H), 7.08 (d, J=17 Hz, 1H), 7.25 (d, J=17 Hz, 1H), 7.50 (t, J=7.7 Hz, 1H), 7.79 (d, J=7.7 Hz, 1H), 8.04 (d, J=7.7 Hz, 1H), 8.31 (s, 1H).

Experiment 3. 4-[2-(3,5-Dihydroxy-4-1-propylphenyl)ethenyl]benzoic acid (6B)

A mixture of 4-[2-(3,5-dimethoxy-4-1-propylphenyl)ethenyl]benzoic acid (0.289 g, 0.886 mmol) and pyridine hydrochloride (0.678, 5.9 mmol) was heated at 200° C. for 2 h under a stream of argon. The reaction mixture was cooled to room temperature. 2NHCl (10 mL) and ether (50 mL) was added. The organic layer was separated and the aqueous mixture was extracted with ether (2×50 mL). The extract was washed with saturated brine and dried over anhydrous Na₂SO₄. Evaporation of ether followed by flash chromatography using ethyl acetate/hexane/acetic acid (40/60/1) afforded the pure acid 6 (0.03 g, 11% yield). ¹HNMR (DMSO-d₆, ppm): δ 1.22 (d, J=7.0 Hz), 6.49 (s, 2H), 6.90 (d, J=18 Hz, 1H), 7.19 (d, J=18 Hz, 1H), 7.67 (d, J=8 Hz, 2H), 7.90 (d, J=8 Hz, 2H), 9.14 (s, 2H).

Experiment 4. 3-[2-(3,5-Dihydroxy-4-1-propylphenyl)ethenyl]benzoic acid (7B)

This material was prepared from 3-[2-(3,5-dimethoxy-4-1-propylphenyl)ethenyl]benzoic acid 2B and pyridine hydrochloride in 86% yield in the same way as described in Example 3. ¹HNMR (DMSO-d₆, ppm): δ 1.22 (d, J=7.0 Hz, 6H), 6.48 (s, 2H), 7.03 (d, J=17 Hz, 1H), 7.12 (d, J=17 Hz, 1H), 7.46 (t, J=7.5 Hz, 1H), 7.7-7.9 (m, 2H), 8.06 (s, 1H), 9.12 (s, 2H).

Experiment 5. 1-(3,5-Dimethoxy-4-1-propylphenyl)-2-phenylethene (19B)

(a) Diethyl benzylphosphonate

The mixture of benzyl bromide (12 mL, 101 mmol) and triethyl phosphite (25 mL, 146 mmol) was heated at 110-130° C. in the presence of Bu₄NI (0.05 g) overnight. The excess triethyl phosphite was removed under reduced pressure at 110° C. The phosphonate (23 g) was obtained quantitatively as a colorless liquid. ¹HNMR (CDCl₃, ppm): δ 1.28 (t, J=7.2 Hz, 6H), 3.20 (d, J=21.9 Hz, 2H), 4.10 (dt., J=7.2 Hz, 7.2 Hz, 4H), 7.30 (s, 5H).

(b) 1-(3,5-Dimethoxy-4-1-propylphenyl)-2-phenylethene (19B)

To a solution of diethyl benzylphosphonate obtained above (11.39 g, 54.7 mmol) in THF (100 mL) at 0° C. was added NaH (60% in mineral oil) (4.68 g, 115 mmol) under N₂. After the addition was completed, the suspension was stirred at 0° C. for 1 h and 3,5-dimethoxy-4-1-propylbenzyl aldehyde obtained in Example 1(c) (11.39 g, 54.7 mmol) in THF (100 mL) was added. The reaction was kept at 0° C. for 1 h and then at 45-50° C. for 5 h. The reaction was cooled to 0° C. Water was added slowly to quench the reaction followed by addition of 2N HCl (75 mL). The mixture was extracted with ether (3×200 mL). The extract was dried over anhydrous Na₂SO₄. Evaporation of ether gave crude 5-(2-phenylethenyl)-2-1-propyl-1,3-dimethoxy benzene (18.07 g). This was used for the next reaction without further purification. A small amount of the crude product was purified by flash chromatography using 10% ethyl acetate in hexane to afford pure product. ¹HNMR (CDCl₃, ppm): δ 1.28 (d, J=7.0 Hz, 6H), 3.58 (hept, J=7.0 Hz, 1H), 3.85 (s, 6H), 6.69 (s, 2H), 7.05 (s, 2H), 7.25 (m, 1H), 7.35 (m, 2H), 7.25 (m, H).

Experiment 6. 5-(2-Phenylethenyl)-2-1-propyl-1,3-benzenediol (20B)

To the crude 1-(3,5-dimethoxy-4-1-propylphenyl)-2-phenylethene (18.07 g) in dry CH₂Cl₂ (100 mL) at −78° C. under N₂ was added BBr₃ (5.2 mL, 55 mmol) dropwise. After the reaction was stirred at −78° C. for 1 h, the temperature was allowed to rise to room temperature and the reaction mixture was stirred at room temperature for 2 days. Water was added to quench the reaction, followed by 20% NaOH to adjust pH>12. The organic layer was removed and the aqueous layer was washed with hexane (2×100 mL). The aqueous layer was acidified with 6N HCl to pH 1 and extracted with ether (3×200 mL). The organic layer was separated and washed with water (50 mL) and brine (50 mL) and dried over anhydrous $Na_2SO_4$. Evaporation of ether gave a red syrup. Recrystallization with chloroform yielded pure stilbene product 20B (6.92 g) as a white crystal. The mother liquid was concentrated and the residue was recrystallized once more to afford an additional 2.5 g of 20B (total 9.42 g, 67.7% over two steps). $^1$HNMR ($CDCl_3$, ppm): δ 1.38 (d, J=7.3 Hz, 6H), 3.46 (hept., J=7.3 Hz, 1H), 4.80 (s, 2H), 6.50 (s, 2H), 6.92 (d, J=17.2 Hz, 1H), 6.97 (d, J=17.2 Hz, 1H), 7.25 (m, 1H), 7.34 (m, 2H), 7.52 (m, 2H).

Experiment 7. 3-Acetoxy-5-(2-phenylethenyl)-2-1-propylphenyl acetate (10B)

To 5-(2-Phenylethenyl)-2-1-propyl-1,3-benzenediol obtained in Example 11 (1.00 g, 3.93 mmol) and triethylamine (1.5 mL, 10.8 mmol) in dichloromethane (100 mL) at 0° C. was added acetyl chloride dropwise. The reaction was monitored by TLC. Water (50 mL) was added after the reaction was complete (~30 min.). The organic layer was separated and washed with 2NHCl (30 mL), $H_2O$ (50 mL), saturated $NaHCO_3$ (50 mL), $H_2O$ (50 mL) and brine (50 mL), and dried over anhydrous sodium sulfate. Evaporation of the solution followed by flash chromatography using 5% ethyl acetate in hexane yielded 3-acetoxy-5-(2-phenylethenyl)-2-1-propylphenyl acetate. (1.32 g, 92%) as a white solid. $^1$HNMR ($CDCl_3$, ppm): δ 1.26 (d, J=7.0 Hz, 6H), 2.35 (s, 6H), 3.08 (hept., J=7.0 Hz, 1H), 6.98 (d, J=17.4 Hz, 1H), 7.04 (d, J=17.4 Hz, 1H), 7.07 (s, 2H), 7.24-7.29 (m, 1H), 7.34-7.38 (m, 2H), 7.45-7.49 (m, 2H).

Experiment 8. 3-Chloroacetoxy-5-(2-phenylethenyl)-2-1-propylphenyl chloroacetate (11B)

This material was synthesized from anhydrous chloroacetic and 5-(2-Phenylethenyl)-2-1-propyl-1,3-benzenediol obtained in Example 11 in 72% yield by the same procedure as described in Example 12. $^1$HNMR ($CDCl_3$, ppm): δ 1.30 (d, J=7.0 Hz, 6H), 3.08 (hept, J=7.0 Hz, 1H), 4.39 (s, 4H), 6.96 (d, J=17 Hz, 1H), 7.14 (d, J=17 Hz, 1H) 7.17 (s, 2H), 7.2-7.5 (m, 5H).

Experiment 9. 1-(3,5-Dimethoxy-4-1-propylphenyl)-2-(4-methoxyphenyl)ethene (12B)

(a) 3,5-Dimethoxy-4-isopropyl benzyl bromide

To 3,5-Dimethoxy-4-1-propylbenzyl alcohol (12.57 g, 59.8 mmol) in dry ether (100 mL) at 0° C. was added $PBr_3$ (3.0 mL, 31.2 mmol) dropwise under nitrogen. The reaction was monitored by TLC. After the reaction was completed (~4 h), water (180 mL) was added. The organic layer was separated and the aqueous layer was extracted with ether (3×50 mL). The extract was washed with water (20 mL), sat. $Na_2CO_3$ (20 mL), water (20 mL) and brine (20 mL), and dried over anhydrous sodium sulfate. Evaporation of the solution yielded pure bromide (14.93 g, 91.4%) as a white solid. $^1$HNMR ($CDCl_3$, ppm): δ 1.29 (d, J=7.1 Hz, 6H), 3.64 (hept, J=7.1 Hz, 1H), 3.84 (s, 6H), 4.50 (s, 2H), 6.60 (s, 2H).

(b) Diethyl (3,5-dimethoxy-4-1-propylbenzyl)phosphonate

The mixture of 3,5-dimethoxy-4-1-propylbenzyl bromide (5.01 g, 18.3 mmol) and triethyl phosphite (4.7 mL, 27.4 mmol) was heated at 110-130° C. in the presence of $Bu_4NI$ (0.05 g) overnight. The excess triethyl phosphite was removed under reduced pressure at 110° C. to give the phosphonate (5.58 g, 92%). $^1$HNMR ($CDCl_3$, ppm): δ 1.27 (d, J=7.1 Hz, 6H), 1.29 (t, J=7.0 Hz, 6H), 3.12 (d, J=21.5 Hz, 2H), 3.4-3.7 (m, 1H), 3.80 (s, 6H), 4.06 (dt, J=7.1, 7.1 Hz, 4H), 6.50 (d, J=2.6 Hz, 2H).

(c) 1-(3,5-Dimethoxy-4-1-propylphenyl)-2-(4-methoxyphenyl)ethene (12B)

This material was prepared from diethyl(3,5-dimethoxy-4-1-propylbenzyl)phosphonate and 4-anisaldehyde in 63% yield as the same procedure as described in Example 5(b). $^1$H NMR ($CDCl_3$, ppm): δ 1.31 (d, J=7.1 Hz, 6H), 3.51-3.74 (m, 1H), 3.86 (s, 3H), 3.91 (s, 6H), 6.71 (s, 2H), 6.84-7.09 (m, 4H), 7.39-7.60 (m, 2H).

Experiment 10. 5-[2-(4-Hydroxyphenyl)ethenyl]-2-1-propyl-1,3-benzenediol (13B)

This material was prepared from 1-(3,5-dimethoxy-4-1-propylphenyl)-2-(4-methoxyphenyl)ethene and pyridine hydrochloride in 30% yield in the same way as described in Example 3. $^1$H NMR (DMSO-$d_6$, ppm): δ 1.22 (d, J=7.0 Hz, 6H), 3.41 (m, 1H), 6.40 (s, 2H), 6.73 (d, J=6.3 Hz, 4H), 7.33 (s, 1H), 7.41 (s, 1H), 8.98 (s, 2H), 9.51 (s, 1H).

Experiment 11. 1-(3,5-Dimethoxy-4-1-propylphenyl)-2-(3,5-dimethoxyphenyl)e-thene (14B)

This material was prepared from diethyl(3,5-dimethoxy-4-1-propylbenzyl)phosphonate and 3,5-dimethoxybenzaldehyde in 25% yield as the same procedure as described in Example 5(b)

Experiment 12. 5-[2-(3,5-Dihydroxyphenyl)ethenyl]-2-1-propyl-1,3-benzenedio-1 (15B)

This material was prepared from 1-(3,5-dimethoxy-4-1-propylphenyl)2-(3,5-dimethoxyphenyl)ethene and $BBr_3$ by the same procedure as described in Example 11.

Experiment 13. 1-(4-Bromo-3,5-dimethoxyphenyl)-2-phenylethene (21B)

(a) Methyl 4-bromo-3,5-dimethoxybenzoate

This material was synthesized from 4-bromo-3,5-dihydroxybenzoic acid and $Me_2SO_4$ in 95% yield by the same method as described in Example 1(a). $^1$HNMR ($CDCl_3$, ppm): δ 3.96 (s, 3H), 3.99 (s, 6H), 7.28 (s, 2H).

(b) 4-Bromo-3,5-dimethoxybenzyl alcohol

This material was synthesized from methyl 4-bromo-3,5-dimethoxybenzoate obtained above in 85% yield by the same method as described in Example 1(b). $^1$HNMR ($CDCl_3$, ppm): 61.95 (s, 1H), 3.93 (s, 6H), 4.69 (s, 2H), 6.61 (s, 2H).

(c) 4-Bromo-3,5-dimethoxybenzaldehyde

This material was synthesized from 4-bromo-3,5-dimethoxybenzyl alcohol in 75% yield by the same method as described in Example 1(c). $^1$HNMR ($CDCl_3$, ppm): δ 4.02 (s, 6H). 7.11 (s, 2H), 9.97 (s, 1H).

(d) 1-(4-Bromo-3,5-dimethoxyphenyl)-2-1-phenylethene (21B)

This material was synthesized from 4-bromo-3,5-dimethoxybenzyl aldehyde and diethyl benzylphosphonate in 70% yield by the same method as described in Example 5(b). $^1$HNMR (CDCl$_3$, ppm): δ 3.96 (s, 6H), 6.72 (s, 2H), 7.06 (d, J=17 Hz, 1H), 7.11 (d, J=17 Hz, 1H), 7.28 (m, 1H), 7.37 (m, 2H), 7.55 (m, 2H).

Experiment 14.
2-Bromo-5-(2-phenylethenyl)-1,3-benzenediol (22B)

This material was synthesized from 1-(4-bromo-3,5-dimethoxyphenyl)-2-phenylethene (21B) and BBr$_3$ in 90% yield by the same method as described in Example 6. $^1$HNMR (CDCl$_3$, ppm): δ 5.39 (s, 2H), 6.81 (s, 2H), 7.06 (d, J=17 Hz, 1H), 7.11 (d, J=17 Hz, 1H), 7.28 (m, 1H), 7.37 (m, 2H), 7.55 (m, 2H).

Experiment 15. 1-[2,5-Dimethoxy-4-(2-phenylethenyl)]phenyl-1-phenylmethanol (16B)

To a solution of 1-(4-bromo-3,5-dimethoxyphenyl)-2-phenylethene (0.2185 g. 0.6845 mmol) in dry THF (10 mL) at −78° C. was added BuLi (0.3 mL, 2.5M in hexane, 0.7530 mmol). One hour after the addition, benzaldehyde (0.07 mL, 0.69 mmol) was added. The reaction mixture was stirred at −78° C. for another 4 hours and then water (12 mL) was added to quench the reaction. This was extracted with ether (3×20 mL). The extract were combined and dried over anhydrous Na$_2$SO$_4$. Evaporation of solvent followed by flash chromatography using 5% ethyl acetate in hexane afforded pure 16B (0.203, 86% yield) as a yellow solid. The $^1$HNMR (CDCl$_3$, ppm): δ 3.88 (s, 6H), 4.26 (d, J=5.6 Hz, 1H), 6.40 (br, 1H), 6.79 (s, 2H), 7.12 (s, 2H), 7.2-7.6 (m, 10H).

Experiment 16.
2,5-Dimethoxy-4-(2-phenylethenyl)benzaldehyde (17B)

This compound was synthesized from 1-(4-bromo-3,5-dimethoxyphenyl)-2-phenylethene, BuLi and N,N-dimethylformamide in 38% yield by the same method as described in Example 15. $^1$HNMR (CDCl$_3$, ppm): δ 3.94 (s, 3H), 4.00 (s, 3H), 6.75 (s, 2H), 7.14 (s, 2H), 7.3-7.5 (m, 5H), 10.52 (s, 1H).

Experiment 17.
1-(3,5-Dimethoxy-4-ethylphenyl)-2-phenylethene (23B)

To a solution of 1-(4-bromo-3,5-dimethoxyphenyl)-2-phenylethene (0.53 g, 1.7 mmol) in THF (10 mL) was added t-Butyl Li (1.1 mL, 1M in THF) at −78° C. After the addition complete, the solution was slowly heated to reflux for 30 min and then cooled down to −78° C. Ethyl iodide (1.2 eq, 0.27 mL) was added to the solution. Water (10 mL) was added after the completion of the reaction. THF was evaporated and the mixture was extracted with CH$_2$Cl$_2$ (3×5 mL). The extract was combined and dried over anhydrous magnesium sulfate. Evaporation of the solution followed by flash chromatography using 20% ether in hexane gave 1,3-dimethoxy-2-ethyl-5-(2-phenylethenyl)benzene in 70% yield. $^1$HNMR (CDCl$_3$, ppm): δ 1.12 (t, J=7.2 Hz, 6H), 2.70 (q, J=7.2 Hz, 2H), 3.91 (s, 6H), 6.74 (s, 2H), 7.07 (s, 2H), 7.26 (m, 1H), 7.36 (m, 2H), 7.52 (m, 2H).

Experiment 18.
2-Ethyl-5-(2-phenylethenyl)-1,3-benzenediol (24B)

This material was synthesized from 1-(3,5-dimethoxy-4-ethylphenyl)-2-phenylethene and BBr$_3$ in 91% yield by the same method as described in Example 6. $^1$HNMR (CDCl$_3$, ppm): δ 1.22 (t, J=7.5 Hz, 6H), 2.70 (q, J=7.5 Hz, 2H), 4.81 (s, 2H), 6.60 (s, 2H), 7.00 (s, 2H), 7.26 (m, 1H), 7.36 (m, 2H), 7.52 (m, 2H).

Experiment 19. 1-(3,5-Dimethoxy-4-n-tetradecanylphenyl)-2-phenylethene (25B)

This material was prepared from 2-bromo-1,3-dimethoxy-5-(2-phenylethenyl)benzene and 1-bromo-n-tetradecane by the same procedure as described in Example 15. $^1$HNMR (CDCl$_3$, ppm): δ 0.91 (m, 6H), 1.29 (m, 22H), 2.65 (m, 2H), 3.90 (s, 6H), 6.73 (s, 2H), 7.10 (s, 2H), 7.26 (m, 1H), 7.36 (m, 2H), 7.52 (m, 2H).

Experiment 20. 5-(2-Phenylethenyl)-2-n-tetradecanyl-1,3-benzenediol (26B)

This material was synthesized from 1-(3,5-dimethoxy-4-n-tetradecanylphenyl)-2-phenylethene and BBr$_3$ by the same method as described in Example 6. $^1$HNMR (CDCl$_3$, ppm): δ 0.95 (m, 6H), 1.30 (m, 22H), 2.65 (m, 2H), 4.80 (s, 2H), 6.60 (s, 2H), 7.00 (s, 2H), 7.26 (m, 1H), 7.36 (m, 2H), 7.52 (m, 2H).

Experiment 21. 2-(3,5-Dimethoxy-4-1-propylphenyl)-1-(2-fluorophenyl)ethene (27)

To a solution of diethyl(3,5-dimethoxy-4-1-propylbenzyl)phosphonate (0.50 g, 1.5 mmol) in THF (10 mL) at 0° C. was added NaH (60% in mineral oil) (0.14 g, 3.5 mmol) under N$_2$. After the addition was completed, the suspension was stirred at 0° C. for 1 h and then 2-fluorobenzaldehyde (0.2 mL, 1.9 mmol) in THF (10 mL) was added. The reaction was kept at 0° C. for 1 h and then at 50° C. for 5 h. The reaction was cooled to 0° C. Water (5 mL) was added slowly to quench the reaction followed by addition of 2N HCl (8 mL). The mixture was extracted with ether (3×20 mL). The extract was dried over anhydrous Na$_2$SO$_4$. Evaporation of ether followed by flash chromatography using 5% ethyl acetate in hexane as eluent afforded 2-(3,5-dimethoxy-4-1-propylphenyl)-1-(2-fluorophenyl)ethene (1). (0.31 g, 68%) as a yellow crystal. $^1$HNMR (CDCl$_3$, ppm): δ 1.34 (d, J=7.1 Hz, 6H), 3.60 (qint. J=7.1 Hz, 1H), 3.89 (s, 6H), 6.74 (s, 2H), 7.0-7.2 (m, 5H), 7.4-7.6 (m, 1H).

Experiment 22. 1-(3,5-Dimethoxy-4-1-propylphenyl)-2-(3-fluorophenyl)ethene (28B)

This material was prepared from diethyl(3,5-dimethoxy-4-1-propylbenzyl)phosphonate and 3-fluorobenzaldehyde in the same way as described in Example 21.

Experiment 23. 1-(3,5-Dimethoxy-4-1-propylphenyl)-2-(4-fluorophenyl)ethene (29B)

This material was prepared from diethyl(3,5-dimethoxy-4-1-propylbenzyl) phosphonate and 4-fluorobenzaldehyde in the same procedure as described in Example 21.

Experiment 24. 2-(3,5-Difluorophenyl)-1-(3,5-dimethoxy-4-1-propylphenyl)ethene (30B)

This material was prepared from (3,5-dimethoxy-4-1-propylbenzyl)phosphonate and 3,5-difluorobenzaldehyde in 27% yield in the same way as described in Example 21.

¹HNMR (CDCl₃, ppm): δ 1.32 (d, J=7.0 Hz, 6H), 3.66 (qint., J=7.0 Hz, 1H), 3.90 (s, 6H), 6.72 (s, 2H), 6.8-7.2 (m, 5H).

Experiment 25. 1-(2,4-Difluorophenyl)-2-(3,5-dimethoxy-4-1-propylphenyl)ethene (31B) (3,5-Dimethoxy-4-1-propylphenyl)ethane To a suspension of methyltriphenylphosphonium bromide (6.89 g, 19.3 mmol) in THF (100 mL) under argon was added BuLi (7.7 ml, 2.5M in hexane, 19.3 mmol) at room temperature. The resultant red solution was stirred for 10 min. and then 3,5-dimethoxy-4-1-propylbenzylaldehyde (4.02 g, 19.3 mmol) obtained above in THF (20 mL) was added. After 2 hours, the reaction was quenched with water (20 mL). The mixture was extracted with ether (3×100 mL). The extract was washed with saturated saline solution (3×30 mL) and dried over sodium sulphate. Evaporation of ether followed by flash chromatography using 3% ethyl acetate in hexane afforded pure (3,5-dimethoxy-4-1-propylphenyl)ethene (2.64 g, 66% yield) as a colorless solid. ¹HNMR (CDCl₃, ppm): δ 1.31 (d, J=7.1 Hz, 6H), 3.61 (qint, J=7.1 Hz, 1H), 3.86 (s, 6H), 5.25 (d, J=1 Hz, 1H), 5.73 (d, J=17 Hz, 1H), 6.64 (s, 2H), 6.70 (dd, J=11, 17 Hz, 1H).

A mixture of (3,5-dimethoxy-4-1-propylphenyl)ethene (0.649 g, 3.15 mmol), 1-bromo-2,4-difluorobenzene (1.23 g, 6.37 mmol), dihydrogen di-µ-chlorotetrkis(di-tert-butylphosphinito-KP)dipalladate (0.1409 g, 0.151 mmol), Bu₄NI (0.582 g, 1.58 mmol) and K₂CO₃ (1.45 g, 10.5 mmol) in DMF (10 mL) was heated at 140° C. under argon. After the reaction was complete (6 h), the reaction mixture was poured into water (10 ml). The aqueous was acidified with 2NHCl and extracted with ether (2×50 mL). The extract was washed with saturated sodium chloride and then dried over anhydrous Na₂SO₄. Evaporation of ether followed by flash chromatography using 2% ethyl acetate in hexane afforded 1-(2,4-difluorophenyl)-2-(3,5-d-imethoxy-4-1-propylphenyl)ethene (31) quantitatively as a yellowish crystal. ¹HNMR (CDCl₃, ppm): δ 1.32 (d, J=7.1 Hz, 6H), 3.63 (qint, J=7.1 Hz, 1H), 3.90 (s, 6H), 6.76 (s, 2H), 7.08 (d, J=17 Hz, 1H), 7.27 (d, J=17 Hz, 1H), 7.63 (d, J=8 Hz, 2H), 8.13 (d, J=8 Hz, 2H).

Experiment 26. 1-(2,6-Difluorophenyl)-2-(3,5-dimethoxy-4-1-propylphenyl)ethene (32B)

This compound was synthesized from (3,5-dimethoxy-4-1-propylphenyl)-ethene and 1-bromo-2,6-difluorobenzene quantitatively in the same procedure as described in preparation of 31B. ¹HNMR (CDCl₃, ppm): δ 1.32 (d, J=7.1 Hz, 6H), 3.62 (qint, J=7.1 Hz, 1H), 3.90 (s, 6H), 6.73 (s, 2H), 6.8-7.2 (m, 4H), 7.41 (d, J=16.6 Hz, 1H).

Experiment 27. 1-(3,5-Dimethoxy-4-1-propylphenyl)-2-(2,4,6-trifluorophenyl)ethene (33B)

This compound was synthesized from (3,5-dimethoxy-4-1-propylphenyl)ethene and 1-bromo-2,4,6-trifluorobenzene in 58% yield in the same procedure as described in preparation of 31B. ¹HNMR (CDCl₃, ppm): δ 1.32 (d, J=7.0 Hz, 6H), 3.62 (qint, J=7.1 Hz, 1H), 3.89 (s, 6H), 6.73 (s, 2H), 6.79-7.55 (m, 4H).

Experiment 28. 1-(3,5-Dimethoxy-4-1-propylphenyl)-2-(2,3,4,5,6-pentafluorophenyl)ethene (34B)

This compound was synthesized from (3,5-dimethoxy-4-1-propylphenyl)ethene and 1-bromo-2,3,4,5,6-trifluorobenzene in the same procedure as described in preparation of 31B. Experiment 29. 5-[2-(2-Fluorophenyl)ethenyl]-2-1-propyl-1,3-benzenediol (37B).

A mixture of 2-(3,5-dimethoxy-4-1-propylphenyl)-1-(2-fluorophenyl)ethene (27B) (0.308 g, 1.03 mmol) and pyridine hydrochloride (0.72 g, 6.2 mmol) was heated at 200° C. for 4 h under a stream of argon. The reaction mixture was cooled to room temperature. 2NHCl (10 mL) and ether (15 mL) was added. The organic layer was separated and the aqueous layer was extracted with ether (3×10 mL). The extract was dried over anhydrous Na₂SO₄. Evaporation of ether followed by flash chromatography using 15% ethyl acetate in hexane afforded pure 5-[2-(2-fluorophenyl)ethenyl]-2-1-propyl-1,3-benzenediol (37B) (0.269 g, 95% yield) as an off-white solid. ¹HNMR (CDCl₃, ppm): δ 1.41 (d, J=7.2 Hz, 6H), 3.51 (qint., J=7.2 Hz, 1H), 5.01 (b, 2H), 6.56 (s, 2H), 6.98 (d, J=17.6 Hz, 1H), 7.0-7.3 (m, 4H), 7.60 (ddd, J=7.5, 7.5, 2.2 Hz, 1H).

Experiment 30. 5-[2-(3-Fluorophenyl)ethenyl]-2-1-propylphenyl-1,3-diol (38B)

This material was prepared from 1-(3,5-dimethoxy-4-1-propylphenyl)-2-(3-fluorophenyl)ethene (28B) and pyridine hydrochloride in the same procedure as described in Example 34. ¹HNMR (CDCl₃, ppm): δ 1.41 (d, 7.2 Hz, 6H), 3.49 (qint., J=7.2 Hz, 1H), 6.53 (s, 2H), 6.9-7.5 (m, 6H).

Experiment 31. 5-[2-(4-Fluorophenyl)ethenyl]-2-1-propylphenyl-1,3-diol (39B)

This material was prepared from 1-(3,5-dimethoxy-4-1-propylphenyl)-2-(4-fluorophenyl)ethene 29B and pyridine hydrochloride (38% yield over 2 steps) in the same procedure as described in Example 34. ¹HNMR (CDCl₃, ppm): δ 1.41 (d, 7.2 Hz, 6H), 3.48 (qint., J=7.2 Hz, 1H), 6.52 (s, 2H), 6.81 (d, J=17 Hz, 1H), 7.00 (d, J=17 Hz, 1H), 7.0-7.2 (m, 2H), 7.4-7.6 (m, 2H); ¹HNMR (DMSO-d₆, ppm): δ 1.22 (d, J=7.1 Hz, 6H), 3.35 (qint., J=7.1 Hz, 1H), 6.45 (s, 2H), 6.81 (d, J=16.7 Hz, 1H), 6.99 (d, J=16.7 Hz, 1H), 7.17 (dd, J=8.8, 8.8 Hz, 2H), 7.61 (dd, J=8.8 Hz, 5.6 Hz, 2H), 9.05 (s, 2H).

Experiment 32. 5-[2-(3,5-Difluorophenyl)ethenyl]-2-1-propylphenyl-1,3-diol (40B)

This material was prepared from 1-(3,5-dimethoxy-4-1-propylphenyl)-2-(3,5-difluorophenyl)ethene and pyridine hydrochloride in 70% yield in the same procedure as described in Example 34. ¹HNMR (CDCl₃, ppm): δ 1.40 (d, J=7.1 Hz, 6H), 3.56 (qint., J=7.2 Hz, 1H), 4.90 (s, 2H), 6.52 (s, 2H), 6.2-7.1 (m, 5H).

Experiment 33. 5-[2-(2,4-Difluorophenyl)ethenyl]-2-1-propyl-1,3-benzenediol (41B)

This material was prepared from 1-(2,4-difluorophenyl)-2-(3,5-dimethoxy-4-1-propylphenyl)ethene and pyridine hydrochloride in 44% yield in the same way as described in Example 34. ¹HNMR (CDCl₃, ppm): δ 1.41 (d, J=7.1 Hz, 6H), 3.49 (qint, J=7.1 Hz, 1H), 4.78 (br, 2H), 6.54 (s, 2H), 6.69-7.02 (m, 3H), 7.13 (d, J=16 Hz, 1H), 7.41-7.75 (m, 1H).

Experiment 34. 5-[2-(2,6-Difluorophenyl)ethenyl]-2-1-propyl-1,3-benzenediol (42B)

This material was prepared from 1-(2,6-difluorophenyl)-2-(3,5-dimethoxy-4-1-propylphenyl)ethene and pyridine hydrochloride in 29% yield in the same way as described in Example 34. ¹HNMR (CDCl₃, ppm): δ 1.42 (d, J=7.1 Hz, 6H), 3.50 (qint, J=7.1 Hz, 1H), 4.77 (br, 2H), 6.57 (s, 2H), 6.8-7.4 (m, 5H).

Experiment 35. 2-i-Propyl-5-[2-(2,4,6-trifluorophenyl)ethenyl]-1,3-benzenediol (43B)

This material was prepared from 1-(3,5-dimethoxy-4-1-propylphenyl)2-(2,4,6-trifluorophenyl)ethene and pyridine hydrochloride in 14% yield in the same way as described in Example 29. ¹HNMR (CDCl₃, ppm): δ 1.42 (d, J=7.1 Hz, 6H), 3.50 (qint, J=7.1 Hz, 1H), 4.77 (br, 2H), 6.55 (s, 2H), 6.59-7.24 (m, 4H).

Experiment 36. 5-[2-(2,3,4,5,6-Pentafluorophenyl)ethenyl]-2-1-propyl-1,3-benzenediol (44B)

This material was prepared from 1-(2,3,4,5,6-pentafluorophenyl)-2-(−3,5-dimethoxy-4-1-propylphenyl)ethene and pyridine hydrochloride in 21% yield in the same way as described in Example 34. ¹HNMR (CDCl₃, ppm): δ 1.40 (d, J=7.2 Hz, 6H), 3.53 (d, J=7.2 Hz, 6H), 4.91 (s, 2H), 6.55 (s, 2H), 6.86 (d, J=17 Hz, 1H), 7.28 (d, J=17 Hz, 1H).

Example 3

Formulations of the Inventive Compounds (a) Ointment Formulation.

Active ingredient (compound of the invention) 0.05-20.0 mg; Ethanol 100 μl; Mineral Oil, USP 50.0 mg and White Petrolatum, USP to make 1.0 g. Procedure: A weighed quantity of white petrolatum and mineral oil are heated to 65° C. and uniformly mixed. The mixture is cooled to 50-55° C. with stirring. The stated active ingredient which has been dissolved in ethanol and milled is added to the above with stirring. The ointment is cooled to room temperature.

(b) Lotion Formulation.

Active ingredient (compound of the invention) 0.05-20.0 mg; Ethanol 100 μl; Micronized Aluminum Monostearate 50.0 mg and Isopropyl Myristate to make 1.0 g. Procedure: Heat about 90% of required isopropyl myristate to 60° C. Add aluminum monostearate with stirring and maintain heat to dissolve aluminum monostearate. Add the stated active ingredient dissolved in ethanol in the remaining quantity of isopropyl myristate. Add with stirring the solution of the stated active ingredient to the thickened solution of aluminum monostearate in isopropylmyristate previously cooled to 45° C. The lotion is cooled to room temperature with agitation.

(c) Gel Formulation.

Active ingredient (compound of the invention) 0.05-20.0 mg; Ethanol 100 μl; Polyethylenes and Copolymers (A-C8) 100.0 mg and Light Mineral Oil to make 1.0 g. Procedure: Add a portion of mineral oil (about 90%) in a suitable vessel. Heat to about 80° C. Add polyethylene (A-C8) to the mineral oil. The mixture is agitated slowly while hot until all the polyethylene is dissolved. Cool the above mixture quickly by placing the vessel in a cooling bath of 10-15° C. and resume the agitation at normal speed. Once the content of the vessel reaches approximately 45° C., add a mixture of the stated active ingredient which was dissolved in ethanol to the above polymer solution. Allow the mixture to air cool with slow agitation. This will result in a gel form.

(d) Cream

Active ingredient (compound of the invention) 0.05-20.0 mg; Ethanol 100 μl and Galax base cream to make 1.0 g. Procedure: A weighed quantity of the stated active ingredient which has been dissolved in 100 μl of ethanol and thoroughly mixed with the Galax base cream at room temperature.

Example 4

Use as an Agent Against Psoriasis and Eczema

The biological activity of the compounds of this invention can be determined by measurement of the effect of the test compound in vivo because there is no animal model suitable for the diseases. The compounds were tested on volunteers. In these tests, representative compound of this invention, i.e., 3,5-dihydroxy-4-isopropylstilbene is active in reducing or eliminating symptoms of psoriasis and eczema.

The following examples describe in detail compounds and compositions illustrative of the present invention and methods which have been devised for their preparation. It will be apparent to those skilled in the art that many modifications, both of materials and methods, may be practiced without departing from the purpose and intent of this disclosure.

A 1% cream of 3,5-dihydroxy-4-isopropylstilbene was prepared for tests on volunteers. Three volunteers, each with a long psoriasis history, were recruited for the tests. Neither of them was on any medication a month before the initiation of the test.

Volunteer 1, Male, 48 years old with scalp psoriasis for more than 15 years. He had used various conventional drugs and treatments, include, steroids, phototherapy and other medicine during the course of his illness. All of these treatments had no or very limited effect on this psoriasis.

Volunteer 2, Female, 24 years old with plaques on her back. She had used hydrocortisone before and stopped using it because of side effects.

Volunteer 3, Male, 35 years old, had an unspecific type of eczema with 3,000 cm² affected area on the trunk and extremities.

The volunteers were treated once per day by applying the creams once per day on top of the affected area with the basic cream as the control (except for volunteer 3). Two comparable body areas were chosen, and one was treated with the control and the other with the cream containing the compound of the invention. The cream of the invention contained 1% 3,5-dihydroxy-4-isopropylstilbene. The control cream was identical except that it contained no 3,5-dihydroxy-4-isopropylstilbene. Each cream was rubbed into the skin in the area to be treated until no more could be rubbed in.

Results: the inventive compound showed great efficacy on the volunteers treated in comparison with the untreated areas and before and after treatment. In the case of volunteer 1, the area applied with the inventive compound started showing improvement in the inflammation and a decrease in proliferative cells three days after the treatment and completely clearance in 7 days. No change occurred in the condition of the area treated with the control cream. In the case of volunteer 2, there was visible improvement in inflammation and in clearance of the proliferative cells three days after the treatment and significant improvement of the psoriasis were observed within seven days of treatment. In the case of volunteer 3, the cream of 3,5-dihydroxy-4-isopropylstilbene (1%) was applied to the right side, and the control was a steroid cream (triamcinolone acetonide, 0.5%) and applied to the left side. Symptoms on the right side significantly improved by day 3 and the improvement was evidently better than the areas treated with the control. This improvement continued for a week and the disease symptoms completely disappeared by week 2.

Example 5

Use as a Protein Kinase Inhibitor

The specific protein kinase activity of the compounds of the invention is shown by the fact that they are active in the in vitro test described here below.

Test for Protein Kinase Inhibition

DNA-PK was purified from human placenta according to Chan, et al. (1996) and the in vitro assay of the inhibitory activity was done according as outlined below. As a standard protocol, each was prepared in 100% DMSO and the assay was performed at the following conditions: Mix 5 μl of protein kinase solution, 5 μl compound testing solution, 51 μl substrate solution and 5 μl assay dilution buffer (20 mM MOPS, pH7.2, 25 mM β-glycerophosphate, 20 mM MgCl$_2$ 5 mM EGTA, 2 mM EDTA, 1 mM DTT, 1 mM sodium vanadate) in a 96 well microtitre plate. The reaction was started by adding 5 μl of radio-labelled ATP solution (250 μM ATP with 1 μCi of [gamma $^{32}$p] ATP) to the reaction mixture and the plate was incubated at room temperature for 15 min. The reaction was stopped by spotting 10 μl of the reaction mixture onto a 96 well plate containing filter-paper discs. After washing the filter paper plate six times with 1% phosphoric acid, the plate was blow-dried and scintillation fluid was added into each well. The plate was then counted in a scintillation counter. IC$_{50}$ values were calculated from triplicated samples. Table 1 shows the inhibitory activity of two representative compounds: 3,5-Dihydroxy-4-isopropyl-trans-stilbene epoxide and 3,5-dihydroxy-4-isopropyl-trans-stilbene.

TABLE 1

Protein kinase inhibitory activity IC$_{50}$ (mM)

| Kinase | 3,5-Dihydroxy-4-isopropyl-trans-stilbene epoxide | 3,5-dihydroxy-4-isopropyl-trans-stilbene (9A) |
|---|---|---|
| Lck | 0.10 | 0.27 |
| Ck2 | 0.31 | 0.13 |
| DNA-Pk | 0.16 | 0.55 |
| Pim-1 | 0.16 | 0.18 |

As can be appreciated from the activity data shown in Table 1, the compounds according to the invention are endowed with valuable properties of inhibiting protein kinases.

Example 6

Figure 2:
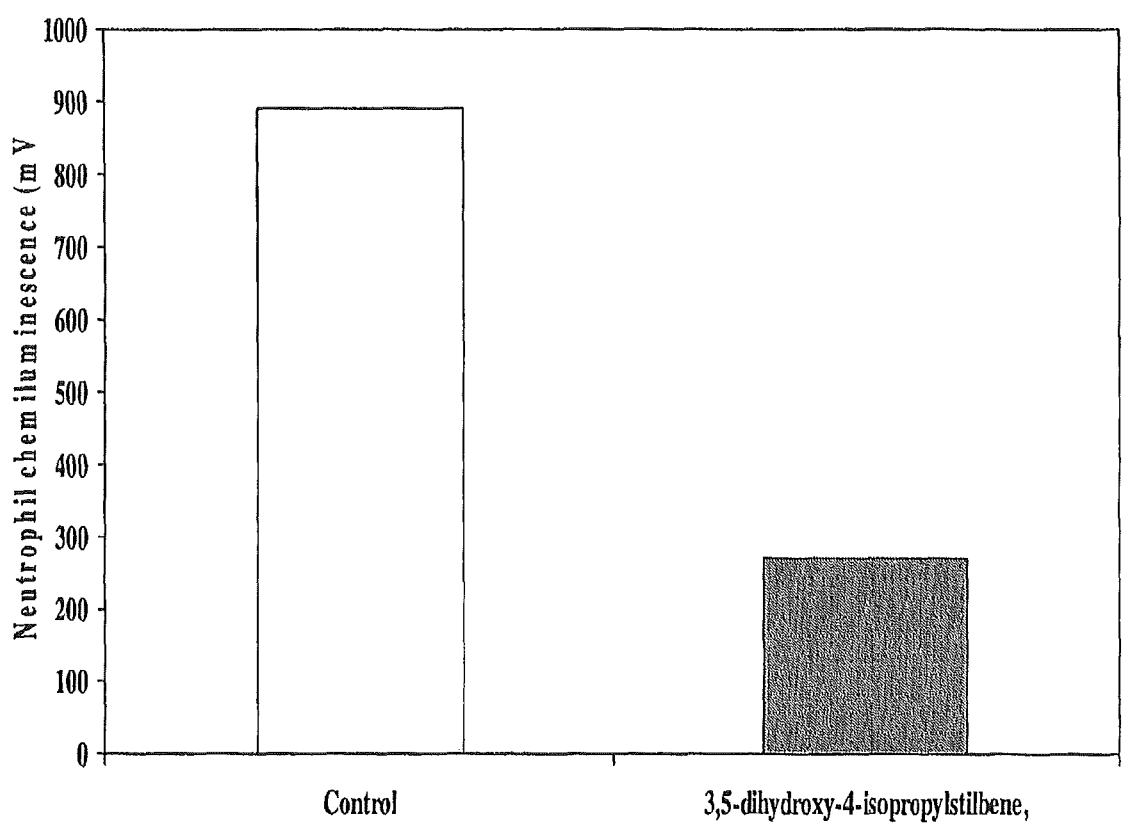
FIG. 2 is a graph showing the effect of 3,5-dihydroxy-4-isopropylstilbene on FMLP induced neutrophil activation.

Use as an Anti-Inflammatory 3,5-dihydroxy-4-isopropylstilbene was tested for inhibitory activity against neutrophil activation by crystal and chemo attractants. Neutrophil activation plays a major role in inflammation. The test was done using an established protocol (Tudan. C. 1999. Bichem Pharmacol 58: 1869-1880). The results are shown in FIGS. 1 and 2.

Example 7

The Biological Activities of Additional Invented Compounds

The standard pharmacological procedures, described fully in the examples hereafter, show the compounds of the invention to inhibit T-cell, keratinocyte proliferation, cell migration induced by leukotriene B4 and to inhibit IFN-γ secretion and VEGF expression in vitro as well as to inhibit TNF-α and edema in vivo.

Experiment 1. Biological Activity of Novel Compounds

These assays for the following biological activities are well-established and known in the art, brief descriptions are provided herein for clarity.

(a). Effect on proliferation and IFN-γ production of human peripheral blood mononuclear cells (PBMC) stimulated by phytochemagglutinin (PHA).

Experiment: PBMC were cultured with PHA and cultured with titrated concentrations of compounds or solvent, or media alone using standard cell culture techniques. The MTT assay was performed after 48 hours of culture. Supernatants were collected after 48 hours of culture and levels of IFN-γ were assayed by ELISA.

Results: 5-[2-(4-Hydroxyphenyl)ethenyl]-2-1-propyl-1,3-benzenediol (13B) of the present invention had an IC$_{50}$ of 2.97 against human PBMC proliferation while resveratrol had an IC$_{50}$ of >50. Compound 13B is 20 times more potent in inhibiting PBMC proliferation (Table 1). Similarly, compound 13B is more than 15 times more potent than is resveratrol in inhibition IFN-γ production (Table 2). Similarly, the three fluorinated compounds, 37B, 38B and 39B had IC$_{50}$<10 PM whereas that of resveratrol was >50 PM the highest concentration tested. The fluorinated compounds had superior activity in inhibiting PBMC proliferation to that of resveratrol with >5 times more potency (Table 2). Similarly, the IC$_{50}$ value of resveratrol is more than 9 times higher than that of the three fluorinated compounds, indicating that the fluorinated compounds are over 9 times more potent than resveratrol in inhibiting IFN-γ production by human PBMC (Table 3).

TABLE 2

Effect of the novel compounds and resveratrol against human PBMC proliferation.

| Compound | IC$_{50}$ (μM) |
|---|---|
| 13B | 2.97 |
| 37B | 5.62 |
| 38B | 9.91 |
| 39B | 7.36 |
| Resveratrol | >50 |

TABLE 3

Effect of the novel compounds and resveratrol on IFN-γ production by human PBMC

| Compound | IFN-γ IC$_{50}$ (μM) |
| --- | --- |
| 13B | 2.55 |
| 37B | 3.80 |
| 38B | 4.29 |
| 39B | 4.16 |
| Resveratrol | 39.2 |

(b) Effect on Human Keratinocyte Proliferation

Human keratinocytes were cultured in the presence of IFN-γ and titrated concentrations of drug or the vehicle. The MTT assay was performed after 48 hours of culture.

Results: Compound 13B had an IC$_{50}$ of 4.3 μM compared to that of resveratrol of >50, indicating compound 13B is more than 10 times potent than is resveratrol (Table 4).

TABLE 4

Effect of the novel compound 13B and resveratrol on human keratinocyte proliferation.

| Compound | IC$_{50}$ (μM) |
| --- | --- |
| 13B | 4.3 |
| resveratrol | >50 |

(c) Effect on Migration of Human White Blood Cells (WBC) Induced by Leukotriene B4 (LTB4)

Experiment: WBC collected from donors was mixed with equal volume of 3% dextran (in 0.15M NaCl). The red blood cells were sedimented (45 minutes, room temperature) and removed. Any remaining red blood cells in the plasma were removed by adding 150 mM of Tris-NH$_4$Cl. The leukocyte-rich plasma was washed twice in Hanks balanced salts solution containing 20 mM HEPES. The WBC was then transferred to RPMI-1640 medium and adjusted to a density of 5×10$^7$ cells/ml. An agarose plate assay system (Nelson et al. 1978) was used to measure the WBC migration. Briefly, a 0.8% agarose solution was prepared with complete RPMI-1640 cell culture medium. About 3.5 ml of this agarose solution was transferred to a glass slide before it solidified. Wells were made on the slide in a 3×6 array fashion (02 mm, inter-well distance 3 mm) once the agarose had solidified. LTB4 was dissolved in anhydrous ethanol to 104 ng/ml and further diluted with the RPMI-1640 medium to 10 ng/ml for the test. Compound 39B was dissolved in DMSO, diluted with RPMI-1640 to 10$^3$ μg/ml and tested at the following concentrations: 100, 10, 1, 0.1 and 0.01 μg/ml. Ten microlitres of cell suspension with different concentrations of compound 39B was added to each well of the center row of the three rows of wells. The same volume of LTB4 in RPMI-1640 medium or the medium alone was added to wells in the other rows and served as controls. After 5 h incubation (5% CO$_2$, 37° C.) the test slides were fixed with 100% methanol (30 min) and dried at 4° C. (overnight). The slides were then examined microscopically. The migration index was defined as the average distances that cells migrated towards the positive LTB4 well divided by that of spontaneous migration. The percentage migration was compared between treatment and the non-drug control. The dose-effect relationship was determined by plotting the percentage chemotaxis vs concentration for IC$_{50}$ values.

Results: Compound 39B inhibited the migration of WBC towards LTB4 in a dose-dependent manner (Table 5).

TABLE 5

Effect of Compound 39B on human white blood cell migration towards LTB4.

| Concentration (μM) | % Migration |
| --- | --- |
| 40 | 13.07 ± 5.8 |
| 8 | 58.46 ± 4.3 |
| 1.6 | 83.85 ± 15.9 |
| 0.32 | 88.46 ± 18.6 |
| 0 | 100 |

Conclusion: Compound 39B showed potent inhibitory activity against WBC migration induced by leukotriene B4, a mediator that plays important role in inflammation, including the auto-immune response.

(d) The Effect on Vascular Endothelial Growth Factor (VEGF) Protein Expression

Experiment: Compound 39B was dissolved in DMSO, diluted with keratinocyte-serum-free medium (KC-SFM) to 10$^3$ μg/ml, further diluted with the culture medium and tested at the following concentrations: 10, 1, 0.1 and 0.01 μg/ml. Prime cultures of keratinocytes were obtained from a commercial source and maintained with KC-SFM at a cell density of 10$^6$/ml. In the test, cells were cultured in 24-well plates and incubated at 37° C. in 5% CO$_2$ first for 4 h, and then treated with rhTGF-α (final concentration 100 ng/ml) and the test compound at different concentrations (0.01-10 μg/ml). Medium without test compound was the negative control. The culture supernatant from each well was separately collected after an additional 24 h incubation and centrifuged at 2000 rpm for 5 minutes before measuring the VEGF concentration. VEGF concentration in the supernatant in each well was calculated based on measurements taken using an ELISA kit, according to the manufacturer's instructions.

Results: Compound 39B showed a dose-dependent effect on the VEGF concentration in the cell supernatant of keratinocytes induced by rhTGF-α after 24-h treatment. This effect increased substantially and the protein concentration decreased 100% when compound 39B concentration increased to 40 μM (Table 6).

TABLE 6

Effect of Compound 39B on VEGF expression of human keratinocytes induced by rhTGF-α

| Concentration (μM) | VEGF (pg/ml) |
| --- | --- |
| 40 | 0 ± 0 |
| 8 | 33.6 ± 1.8 |
| 1.6 | 34.4 ± 2.0 |
| 0 | 38.9 ± 2.8 |

Conclusion: Compound 39B had a significant inhibitory effect on VEGF expression in human keratinocytes.

(e) In Vivo Efficacy in Endotoxemia Mouse Model

The in vivo endotoxemia model used in these studies represents a mouse showing the early inflammatory response. Such severe infection can be caused by Gram negative bacteria may lead to the development of septic shock. This toxicity is caused by the lipopolysaccharide (LPS) component of the bacterial cell wall, and injection of LPS into mice can mimic the physiological response typical of the septic shock syndrome. LPS-mediated toxicity is due to the release of cytokines such as TNF-α, IL-1 and IFN-γ by activated macrophages, and the degree of toxicity can be measured by the level of these cytokines in the blood.

Experiment: Test compounds were dissolved and formulated in 50% PEG-400 in water. Female Balb/c mice (~20 g) were first injected separately intraperitoneally (IP) with 25 mg/kg of each test compound, then challenged by injection with 40 mg/kg lipopolysaccharide (LPS) (IP) 30 minutes later. One drug injection with 12.5 mg/kg of test compound was done at the same time as (LPS challenge and two subsequent sequential injections at 30 minutes intervals. Positive control of dexamethasone was administered in a similar manner starting at 0.4 mg/kg and subsequently 0.2 mg/kg for three additional injections. Mice were sacrificed and blood collected by cardiac puncture 150 minutes after LPS challenge. The serum TNF-α levels were determined by ELISA. Each test group was comprised of six mice. Group of mice injected with the vehicle alone was used as negative control.

Results: Compound 37B and 39B decreased significantly (P<0.05) TNF-α levels in mice blood induced by LPS (Table 7).

TABLE 7

Effect of the novel compounds, 37B and 39B on TNF-α levels induced by LPS in a mouse model.

| Compound | TNF-α (pg/mL) | P-value |
| --- | --- | --- |
| 37B | 638.9 ± 273.0 | 0.03 |
| 39B | 601.6 ± 211.9 | 0.01 |
| Carrier | 1126.6 ± 396.4 | |
| Dexamethasone | 281.3 ± 67.2 | 0.0004 |

P-values calculated with Student's t-test (unpaired, two-tailed)

Conclusions: The fluorinated compounds, compound 37B and 39B significantly decreased levels of TNF-α that modulate a broad range of activities in mice, resulting in reduced inflammatory reactions in animals.

(f) Efficacy on TPA Induced Edema

Experiment: Three representative compounds, 5-(2-phenylethenyl)-2-1-propyl-1,3-benzenediol, as previously reported, a closely related stilbene derivative (WO 0142231) and compound 39B, a novel compound of the current invention, were assayed against the edema on female mice (Balb/c) aged 10-12 weeks, using 0.01% Calcitriol (a commercial standard) as a positive control. Phorbol-12-myristate-13-acetate (TPA) was used as the edema inducer. TPA and the test compounds were all dissolved in 100% ethanol and 20 µl applied on the right ear of the mouse with six mice per group. The TPA concentration used was 0.01% (w/v). Ear thickness was measured 6 hours after TPA treatment to determine if edema was decreased. In each experiment replicated groups of TPA treated mice were treated with either 5-(2-phenylethenyl)-2-1-propyl-1,3-benzenediol, Calcitriol, compound 39B or only ethanol, and the level of inhibition was obtained by measuring the thickness of the ear and expressing the difference in thickness of the treated ear from that of the ethanol treated ear, as a percentage.

Results: The fluorinated compound reduces the edema significantly. With one of H atoms of the previously reported stilbene, 5-(2-phenylethenyl)-2-1-propyl-1,3-benzenediol (9A), replaced by a F to the novel compound 39B of the current invention, the inhibition of edema is increased from 8% to 85% while inhibition of Calcitriol was 31%, demonstrating the surprisingly high levels of activity of the novel compound 39B of the current invention.

TABLE 8

Anti-inflammatory activity of stilbene compound after a single topical administration in the TPA-induced ear edema model

| Treatment | % edema inhibition |
| --- | --- |
| TPA(0.01%) + Compound 9A (0.3%) | 8.0 |
| TPA(0.01%) + Compound 39B (0.3%) | 85.2 |
| TPA(0.01%) + Calcitriol (0.01%) | 31.2 |

To assess the in vivo efficacy for preventive and therapeutic activities of these compounds on IBD, two experiments were designed and tested using the dextran sulfate sodium (DSS) experimental mouse model for human IBD.

For the preventive experiment, compounds 9A and 39B were simultaneously administrated orally with 2% DSS at the dose of 500 mg/kg/day. Vehicle alone and glucocorticoid (dexamethasone 20 mg/kg/day) were used as controls. At day 7, mice were sacrificed, examined for stool appearance, diarrhea and colon macroscopic damage including ulceration, inflammation and adhesion. Colon samples were also taken and fixed in 10% formalin for histological assessment of architecture, ulceration, inflammation and serosal damage.

For the therapeutic experiment a further experiment was done to test different doses of 9A on severe, acute intestinal inflammation in mice induced by a high dose of DSS (5%). In this experiment, drug treatment started from day 3 post DSS induction when disease symptom was established. 9A (200 mg/kg or 100 mg/kg) was administered through oral lavage once daily and a commercial drug, sulfasalazine (SASP, 100 mg/kg/day) was used as positive control. Experiment was terminated at day 7 and the efficacy was assessed.

Figure 3:
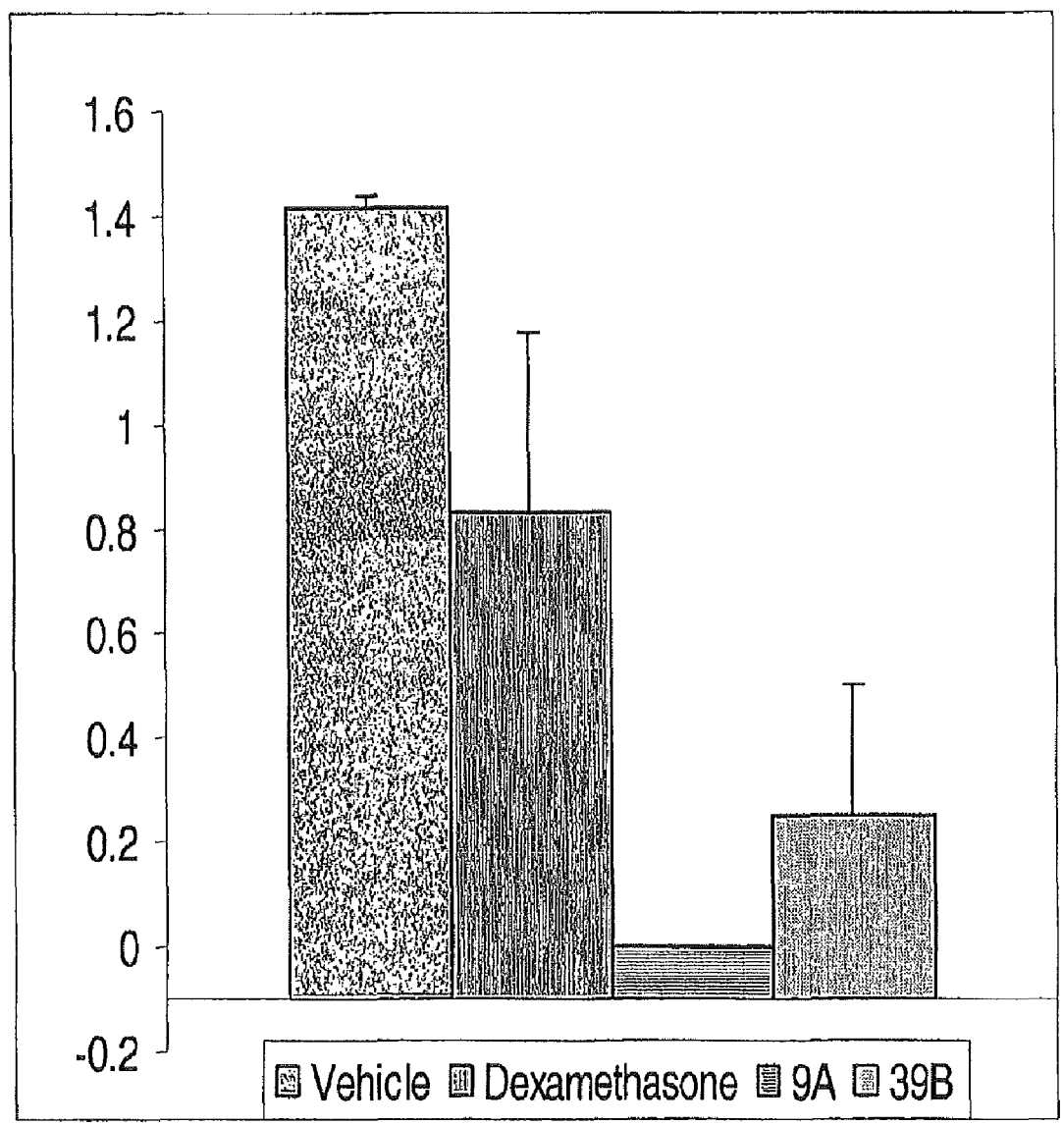
FIG. 3. Macroscopic disease index scores among different treatment groups of mice at the end of the experiment. Macroscopic scores were assessed by examining the stool and colon.
Figure 4:
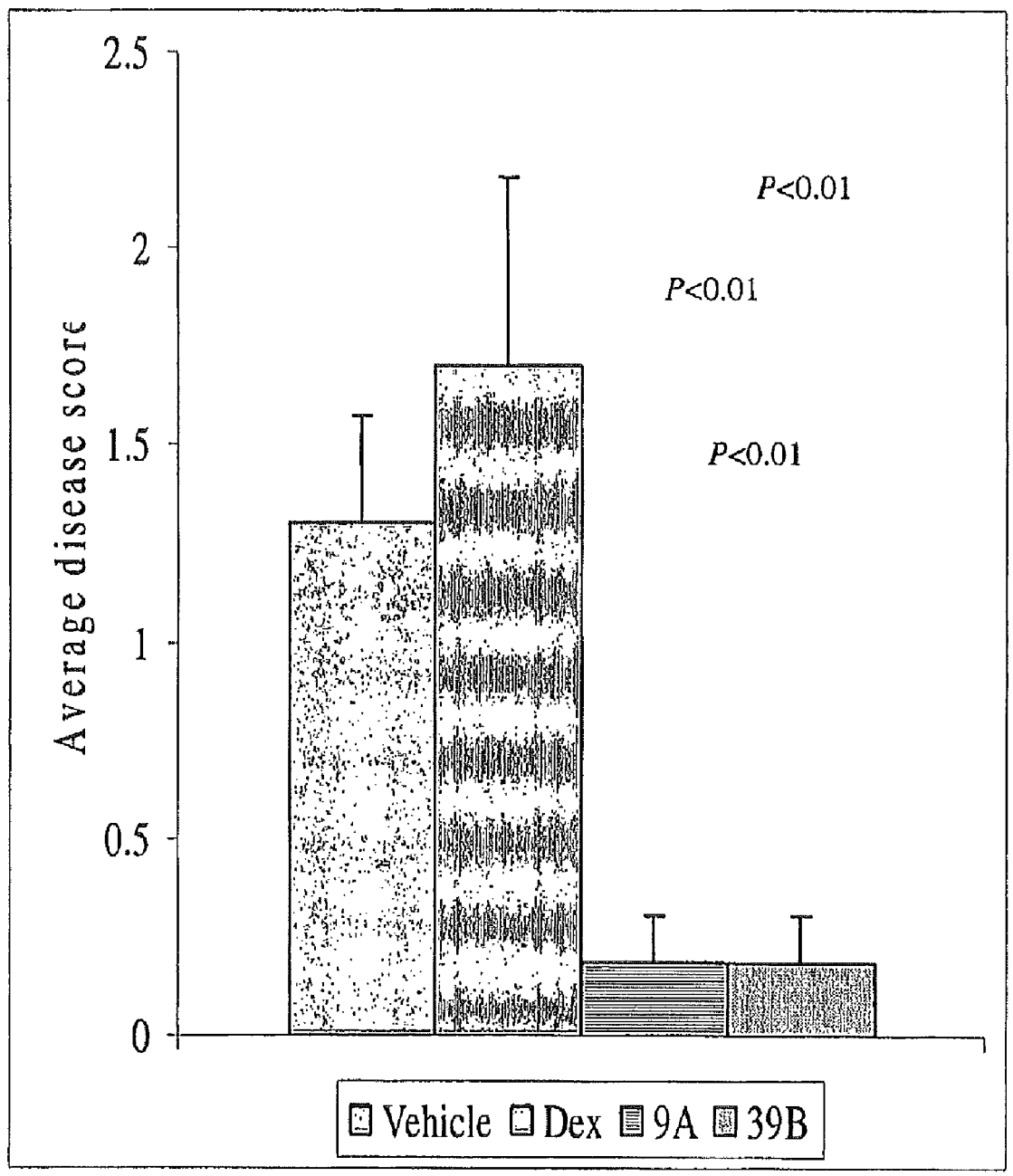
FIG. 4. Total microscopic score of intestinal inflammatory severity at the end of the experiment FIG. 5. Therapeutic effect of 9A and SASP on acute severe colon inflammation induced by 5% DSS in Balb/c mice.
Figure 5:
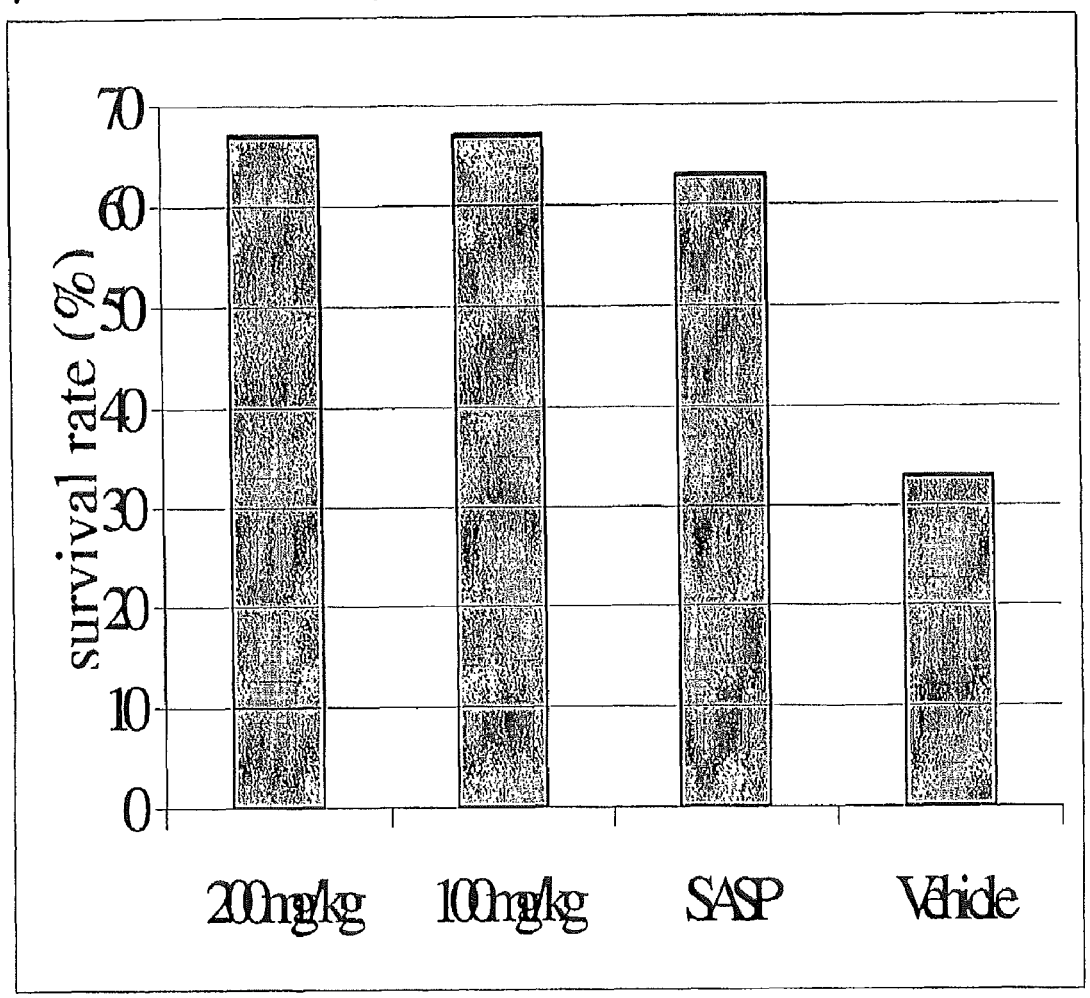

Results: 9A and 39B significantly decreased macroscopic and microscopic diseases scores in the preventive experiment. The preventive activity was significantly better than that of dexamethasone (FIG. 3-4). In the therapeutic experiment, the 9A and SASP treated mice had significantly higher survival rate than those in the control treatment which had severe colon inflammation. Daily treatment of 9A resulted in a survival rate of 67% whereas survival in the vehicle control group was 33% (FIG. 5). The macroscore disease index showed that 9A treatments and the SASP treatment significantly ameliorated diarrheal symptoms (Table 9). Similarly, the bleeding scores of the 9A 200 mg, 100 mg and SASP treatments were significantly lower than that of the vehicle control treatment (Table 9).

Conclusions: The 9A and 39B compounds significantly inhibit gross symptoms and colonic histopathology in BALB/c mice when treated concurrently with DSS (2%) for induction of IBD. In an experiment at a higher level (5%) of DSS induction of IBD 9A ameliorates disease symptoms and increases mouse survival rate as well as the commercial treatment when applied after the disease has been established in the mice. These results indicate that oral administration of these compounds reach the IBD disease site in the colon at effective concentrations that give preventive and therapeutic treatment levels better than that of dexamethasone or similar to a known commercial drug (SASP), the standard treatment of human IBD.

TABLE 9

Effect of different doses of 9A and SASP (100 mg/kg) on acute colon inflammation induced by 5% DSS administration in Balb/c mice. Expressed as mean (.±.SEM) symptom scores** at day seven (n = 9).

| Treatment | Diarrheal score | Bleeding score |
|---|---|---|
| 200 mg/kg | 2.4 ± 0.45* | 3.2 ± 0.49* |
| 100 mg/kg | 2.0 ± 0.73* | 3.3 ± 0.37* |
| SASP | 2.8 ± 0.49* | 3.6 ± 0.24* |
| Vehicle | 4.0 ± 0 | 4.0 ± 0 |

*significantly (P < 0.05) different from the vehicle control.
**diarreal score: 1 = normal, 2 = loose stools, 4 = diarrhea; bleeding score: 1 = normal, 2 = bloody stool, 4 = gross bleeding.

While the invention has been disclosed with respect to preferred embodiments, those skilled in the art will realize that modifications can be made to the specific embodiments exemplified while remaining within the scope of the invention, and that the details of such embodiments are not to be construed as limitations to the invention.

What is claimed is:

1. A method of treating psoriasis comprising administering to a patient a pharmaceutical composition comprising 3,5-dihydroxy-4-isopropylstilbene.

2. A method of treating eczema comprising administering to a patient a pharmaceutical composition comprising 3,5-dihydroxy-4-isopropylstilbene.

3. A method of treating inflammatory disorders comprising administering to a patient a pharmaceutical composition comprising 3,5-dihydroxy-4-isopropylstilbene.

* * * * *